US008909319B2

(12) United States Patent
Larson et al.

(10) Patent No.: US 8,909,319 B2
(45) Date of Patent: Dec. 9, 2014

(54) DEVICE AND METHOD FOR MRI-GUIDED BREAST INTERVENTIONS

(75) Inventors: Blake Timothy Larson, Saint Paul, MN (US); Arthur Guy Erdman, New Brighton, MN (US)

(73) Assignee: MRI Robotics LLC, Saint Paul, MN (US)

( * ) Notice: Subject to any disclaimer, the term of this patent is extended or adjusted under 35 U.S.C. 154(b) by 675 days.

(21) Appl. No.: 12/423,800

(22) Filed: Apr. 14, 2009

(65) Prior Publication Data

US 2009/0259122 A1    Oct. 15, 2009

Related U.S. Application Data

(60) Provisional application No. 61/124,057, filed on Apr. 14, 2008, provisional application No. 61/124,058, filed on Apr. 14, 2008, provisional application No. 61/168,559, filed on Apr. 11, 2009.

(51) Int. Cl.

| *A61B 5/05* | (2006.01) |
|---|---|
| *A61B 5/055* | (2006.01) |
| *A61B 19/00* | (2006.01) |
| *B29C 65/78* | (2006.01) |
| *B23Q 39/00* | (2006.01) |
| *A61B 6/04* | (2006.01) |
| *A61B 8/00* | (2006.01) |
| *A61B 10/02* | (2006.01) |
| *A61B 17/34* | (2006.01) |

(52) U.S. Cl.
CPC ............ *A61B 5/0555* (2013.01); *A61B 19/201* (2013.01); *B65D 2519/00059* (2013.01); *B29C 65/7802* (2013.01); *B23Q 39/00* (2013.01); *A61B 6/0435* (2013.01); *A61B 8/406* (2013.01); *A61B 10/0233* (2013.01); *A61B 2017/3409* (2013.01); *A61B 2019/205* (2013.01)

USPC ........... 600/411; 600/407; 600/415; 600/421; 29/469

(58) Field of Classification Search
USPC .......... 600/407–423; 324/200–243, 306–309, 324/318–322
See application file for complete search history.

(56) References Cited

U.S. PATENT DOCUMENTS 6,558,337 B2    5/2003    Dvorak et al.
6,675,037 B1 *  1/2004    Tsekos ......................... 600/417

(Continued)

OTHER PUBLICATIONS

Doler, Werner, et al., "Stereotaxic add-on device for MR-guided biopsy of breast lesions", "Radiology", 1996, pp. 863-864.

(Continued)

*Primary Examiner* — Unsu Jung
*Assistant Examiner* — Shahdeep Mohammed
(74) *Attorney, Agent, or Firm* — Charles A. Lemaire; Jonathan M. Rixen; Lemaire Patent Law Firm, P.L.L.C.

(57) ABSTRACT

A method and apparatus for radially compressing bodily tissue and performing medical procedures from a selected one of a plurality of circumferential positions and angles, a selected one of a plurality of different elevations and elevational angles. Some embodiments include a tissue-compression fixture having members that are configured to be moved to radially compress bodily tissue such that each of a plurality of areas of biological tissue are exposed between the plurality of members, and wherein the fixture is compatible with use in an MRI machine in operation; an actuator having a receiver for a medical-procedure probe; and a computer system operatively coupled to the actuator to move the probe. The computer receives user commands, and based on the commands, moves the actuator to a selected one of a plurality of different positions around the tissue-compression fixture and then extends the probe into the patient.

20 Claims, 17 Drawing Sheets

(56) References Cited

U.S. PATENT DOCUMENTS

| | | | |
|---|---|---|---|
| 7,171,256 B1* | 1/2007 | Graessle et al. | 600/427 |
| 7,699,783 B2* | 4/2010 | Hanover et al. | 600/459 |
| 7,711,407 B2* | 5/2010 | Hughes et al. | 600/417 |
| 7,769,426 B2* | 8/2010 | Hibner et al. | 600/411 |
| 7,826,883 B2* | 11/2010 | Hibner et al. | 600/407 |
| 7,892,243 B2* | 2/2011 | Stuart | 606/130 |
| 2002/0156365 A1* | 10/2002 | Tsekos | 600/411 |
| 2007/0089557 A1* | 4/2007 | Solomon et al. | 74/490.01 |
| 2007/0167736 A1* | 7/2007 | Dietz et al. | 600/411 |
| 2007/0250047 A1* | 10/2007 | Harter | 606/1 |
| 2008/0065097 A1* | 3/2008 | Duval et al. | 606/130 |
| 2008/0103491 A1* | 5/2008 | Omori et al. | 606/1 |
| 2008/0132913 A1* | 6/2008 | Brock et al. | 606/130 |
| 2008/0234700 A1* | 9/2008 | Trovato et al. | 606/139 |
| 2010/0010504 A1* | 1/2010 | Simaan et al. | 606/130 |

OTHER PUBLICATIONS

Fischer, Uwe, et al, "Magnetic resonance guided localization and biopsy of suspicious breast lesions", "Topics in Magnetic Resonance Imaging", Feb. 1998, pp. 44-59, vol. 9, No. 1.

Kaiser, Werner A., et al, "Robotic system for biopsy and therapy of breast lesions in a high-field whole-body magnetic resonance tomography unit", "Investigative Radiology", Aug. 2000, pp. 513-519, vol. 35.

Kuhl, C.K., et al., "Interventional breast MR imaging: Clinical use of a stereotactic localization and biopsy device", "Radiology", 1997, pp. 667-675, vol. 204.

Larson, Blake T., et al., "Design of a robotic stereotactic device for biopsy and minimally invasive interventions in the breast with real time MRE", "Proceedings of DETC 02: ASME 2002 Design Engineering Technical Conferences and Computers and Information in Engineering Conference", Sep. 29-Oct.

Larson, Blake T., et al., "A Robotic Device for Minimally Invasive Breast Interventions With Real-Time MRI Guidance", "Proceedings of the IEEE 3rd International Symposium on Bioinformatics and Bioengineering (BIBE2003), IEEE", 2003, pp. 190-197.

Larson, Blake T., et al., "Design of an MRI-Compatible Robotic Stereotactic Device for Minimally Invasive Interventions in the Breast", "Journal of Biomechanical Engineering, Transactions of the ASME", Aug. 2004, pp. 459-465, vol. 126.

Larson, Blake T., et al., "An MRI-compatible probe exchanger for early diagnosis and treatment of breast cancer", "Proceedings of the ASME 2004 Design Engineering Technical Conferences and Computers and Information in Engineering Conference, ASME", 2004.

* cited by examiner

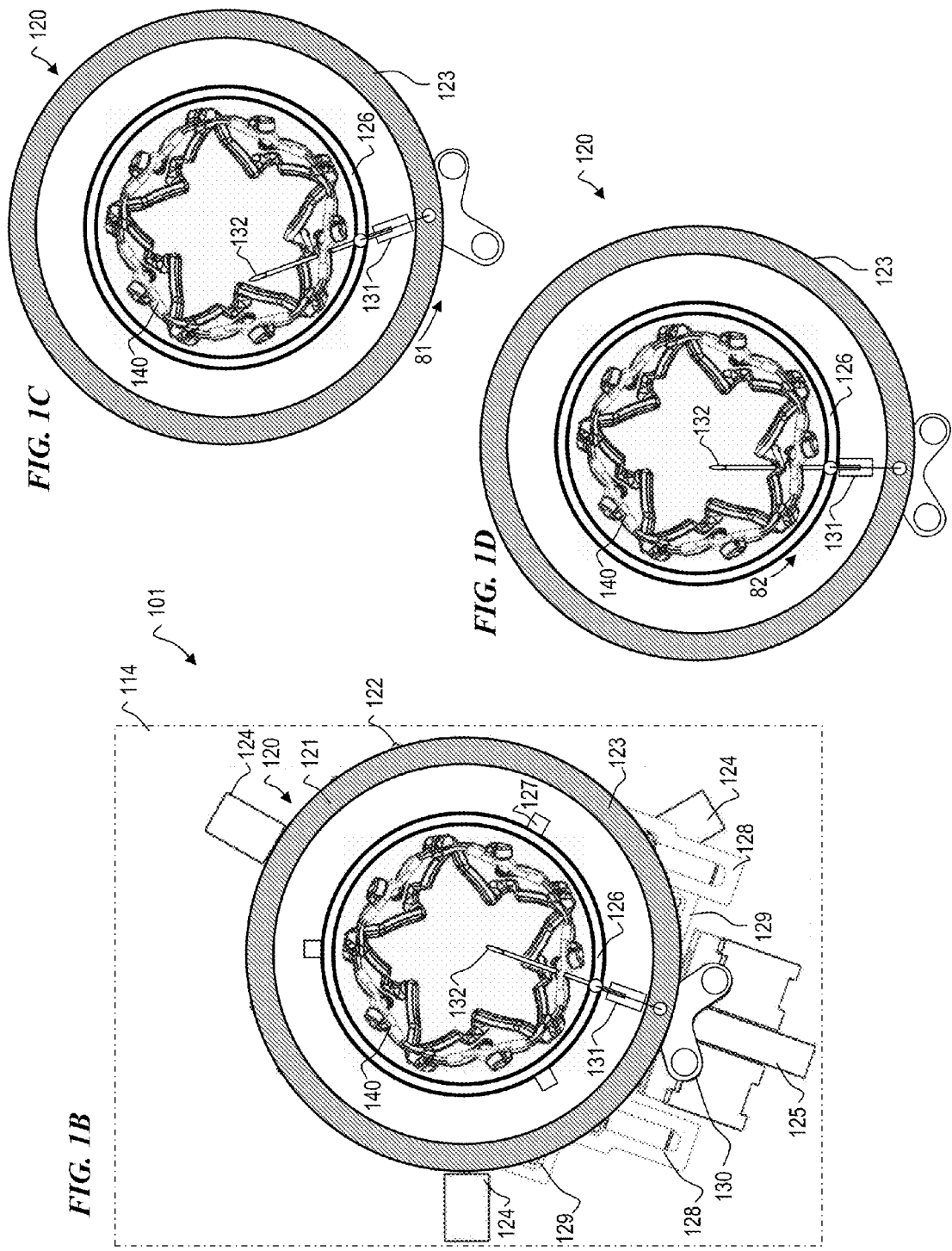

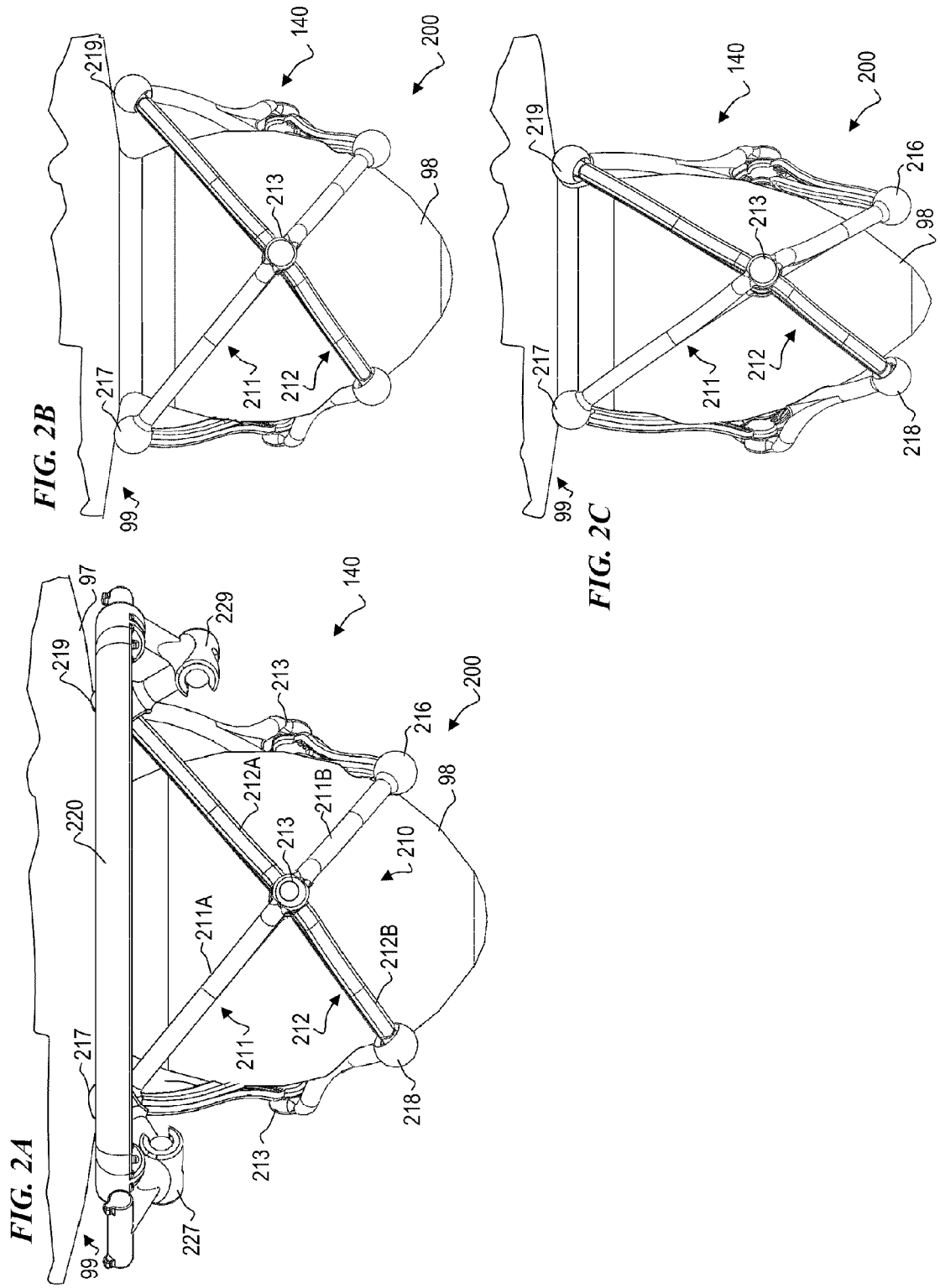

DEVICE AND METHOD FOR MRI-GUIDED BREAST INTERVENTIONS

CROSS-REFERENCE TO RELATED APPLICATIONS

This invention claims benefit under 35 U.S.C. §119(e) of U.S. Provisional Patent Application No. 61/124,058 titled "Device for MRI-guided Breast Intervention" and filed Apr. 14, 2008; U.S. Provisional Patent Application No. 61/124,057 titled "Breast Stabilization Device" and filed Apr. 14, 2008; and of U.S. Provisional Patent Application No. 61/168,559, filed Apr. 11, 2009, which are each hereby incorporated herein in their entirety by reference.

This invention is related to U.S. patent application Ser. No. 12/423,798 titled "TISSUE-STABILIZATION DEVICE AND METHOD FOR MEDICAL PROCEDURES" filed on Apr. 14, 2009 by the inventors of the present invention, which is hereby incorporated herein in its entirety by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of grant number DAMD1703-10397 awarded under the U.S. Army Breast Cancer Research Program.

FIELD OF THE INVENTION

This invention relates to the field of mechanical positioners, and more specifically to a method and apparatus for holding and positioning surgical and/or diagnostic instruments within a body cavity or relative to dissected in-vivo biological tissue of an animal (such as a human) (such as a person's abdominal cavity) to stabilize instruments relative to the surrounding tissue during a medical procedure such as an appendectomy.

BACKGROUND OF THE INVENTION

Several devices have been designed for MRI-guided breast biopsies. U.S. Pat. No. 6,675,037 issued to Nikolaos V. Tsekos on Jan. 6, 2004 titled "MRI-guided interventional mammary procedures" and is incorporated herein by reference. Tsekos discloses a remotely controlled apparatus for MR-guided interventional procedures with four positional degrees of freedom to deliver a probe to a target location within the breast. The apparatus allows the practice of a method that provides flexibility in conditioning the breast, i.e., orientation and degree of compression, and in setting the trajectory of the intervention. To that end, a conditioning/positioning device, fitted with the appropriate degrees of freedom, provides the means for interventional procedures. Remote control of this device can allow planning the operation and performing the relevant tasks in a short period, for example, within the contrast window provided by a single injection of a contrast agent.

U.S. Pat. No. 6,558,337 titled "Positioner for medical devices such as biopsy needles" issued to Dvorak et al. May 6, 2003 and is incorporated herein by reference. Dvorak et al. disclose a similar device with a slightly different method for determining a declination angle of the probe. However, both of these designs are built upon using only bilateral compression plates to stabilize the breast. Not only does this limit access to the breast, there may be movement of the target between uncompressed and compressed states, thereby requiring repositioning and reimaging.

A paper by Blake T. Larson, Nikolaos V. Tsekos, and Arthur G. Erdman, "A Robotic Device For Minimally Invasive Breast Interventions With Real-Time MRI Guidance", Proceedings of the IEEE 3rd International Symposium on Bioinformatics and Bioengineering (BIBE2003), IEEE, pages 190-197, is hereby incorporated by reference. This paper describes a device to perform minimally invasive interventions in the breast with real-time MRI guidance for the early detection and treatment of breast cancer. The device uses five computer-controlled degrees of freedom to perform minimally invasive interventions inside a closed MRI scanner. Typically the intervention would consist of a biopsy of the suspicious lesion for diagnosis, but may involve therapies to destroy or remove malignant tissue in the breast. The procedure proceeds with: (a) conditioning of the breast along a prescribed orientation, (b) definition of an insertion vector by its height and pitch angle, and (c) insertion into the breast. The entire device is made of materials compatible with MRI, avoiding artifacts and distortion of the local magnetic field. The device is remotely controlled via a graphical user interface. This is the first surgical robotic device to perform real-time MRI-guided breast interventions in the United States.

A paper by Blake T. Larson, Nikolaos V. Tsekos, Arthur G. Erdman, Essa Yacoub, Panagiotis V. Tsekos, and Toannis G. Koutlas, "DESIGN OF A ROBOTIC STEREOTACTIC DEVICE FOR BIOPSY AND MINIMALLY INVASIVE INTERVENTIONS IN THE BREAST WITH REAL TIME MRI GUIDANCE" Proceedings of DETC'02: ASME 2002 Design Engineering Technical Conferences and Computers and Information in Engineering Conference, Montreal, Canada, Sep. 29-Oct. 2, 2002 (DETC2002/MECH-34286), is hereby incorporated by reference. This paper described a robotic device to perform biopsy and therapeutic interventions in the breast with real-time MRI guidance. The device used parallel-plate bilateral compression plates to flatten and immobilize the breast of the patient. The device was designed to allow for (i) conditioning of the breast by compression, (ii) definition of the interventional probe trajectory, by setting the height and pitch of a probe insertion apparatus, and (iii) positioning of an interventional probe by setting the depth of insertion. The apparatus was fitted with five computer-controlled degrees of freedom for delivering an interventional procedure. The apparatus was remotely controlled by means of ultrasonic actuators and a graphical user interface, providing real-time MRI-guided planning and monitoring of the operation.

A 2004 paper by Blake T. Larson, Nikolaos V. Tsekos, Essa Yacoub, Panagiotis V. Tsekos, Ioannis G. Koutlas, "Design of an MRI-Compatible Robotic Stereotactic Device for Minimally Invasive Interventions in the Breast," Journal of Biomechanical Engineering, Transactions of the ASME, August 2004, Vol. 126, pages 459-465), is hereby incorporated by reference. This paper described a robotic device to perform biopsy and therapeutic interventions in the breast with real-time magnetic-resonance-imaging (MRI) guidance. The device was designed to allow for (i) stabilization of the breast by compression, (ii) definition of the interventional probe trajectory by setting the height and pitch of a probe insertion apparatus, and (iii) positioning of an interventional probe by setting the depth of insertion. The apparatus is fitted with five computer-controlled degrees of freedom for delivering an interventional procedure. The apparatus is remotely controlled by means of ultrasonic motors and a graphical user interface, providing real-time MRI-guided planning and monitoring of the operation. Joint-motion measurements found probe placement in less than 50 s and sub-millimeter repeatability of the probe tip for same-direction point-to-point movements. However, backlash in the rotation joint may incur probe-tip-positional errors of up to 5 mm at a distance of 40 mm from the rotation axis, which may occur for women with large breasts. The imprecision caused by this backlash becomes negligible as the probe tip nears the rotation axis. Real-time MRI-guidance would allow the physician to correct this error. Compatibility of the device within the MRI environment was successfully tested on a 4-Tesla MRI human scanner.

Other conventional MRI-compatible devices include: W. A. Kaiser, H. Fischer, J. Vagner, and M. Selid, "Robotic system for biopsy and therapy of breast lesions in a high-field whole-body magnetic resonance tomography unit," Investigative Radiology, vol. 35, pp. 513-519, August 2000 (which is incorporated herein by reference), which describes an apparatus with a limited range of motion.

What is needed is an improved motor-controlled positioning and actuating system for performing medical procedures, and in some embodiments, in particular such a system that is compatible for use within a high-magnetic-field environment such as an MRI (magnetic-resonance-imaging) machine.

SUMMARY OF THE INVENTION

In some embodiments, the present invention provides a new MR image-guided interventional (IGI) system with 3D probe-positioning capability and fitted with a custom breast coil (the coil being a portion of the image-data-gathering antenna and electronics subsystem of an MRI machine). To improve the accuracy of probe localization, graphic tools and real-time image guidance is incorporated to calculate the best point of access to the lesions and to verify probe location.

In some embodiments, the present invention provides a method and apparatus for radially compressing bodily tissue and performing medical procedures from a selected one of a plurality of circumferential positions and angles, a selected one of a plurality of different elevations and elevational angles. Some embodiments include a tissue-compression fixture having a plurality of members that are configured to be moved to radially compress bodily tissue such that each of a plurality of areas of biological tissue are exposed between the plurality of members, and wherein the fixture is compatible with use in an MRI machine in operation; an actuator having a receiver for a medical-procedure probe; and a computer system operatively coupled to the actuator to move the probe. The computer receives user commands, and based on the commands, moves the actuator to a selected one of a plurality of different positions around the tissue-compression fixture and then extends the probe into the patient. In some embodiments, the tissue-compression fixture is configured to compress and stabilize breast tissue during a biopsy or other medical intervention on the breast.

In some embodiments, this breast compression and immobilization is achieved using a radial-compression mechanism having a substantially open structure, but with a system of breast-compression struts, that, in some embodiments, also serve as RF coils for receiving image data for the MRI machine. In some embodiments, the computer guidance tracks the position and orientation of the probe (e.g., a biopsy needle) relative to the struts and other obstructions in this system in order to automatically avoid contact and interference with the breast-compression struts when the probe is moved from one position to an other, thus relieving the physician of the need to do this task.

In some embodiments, an image of a virtual slice of the breast tissue is calculated and displayed in substantially real time as if from the viewpoint of the medical-procedure probe (e.g., as if viewed along a longitudinal axis ("down the needle") of a biopsy probe so the physician "sees" what the probe is aiming at), and another image of a virtual slice of the breast tissue is calculated and displayed in substantially real time as if from another viewpoint (e.g., as a side view of the medical-procedure probe, so the physician "sees" how far the probe is away from the lesion at which the probe is aiming). In some such embodiments, the physician moves a cursor or crosshairs to a suspected lesion in the MRI image, and the computer system automatically calculates a position and orientation for the probe that provides an optimal or reasonably short distance to the lesion (e.g., a path that cuts the least-length path from the skin, while avoiding interference with the compression elements of the tissue-compression fixture and/or other obstructions). Some embodiments further elicit and receive user input (e.g., from a physician) that indicate particular regions or body structures of the patient (such as nerves) that the physician wants to avoid damaging, and the computer then calculates a probe path to avoid these structures as well as avoiding interference with structures of the apparatus, and then maneuvers the probe to a position, height, and angular orientation that provides probe movement along that calculated path.

BRIEF DESCRIPTION OF THE DRAWINGS

FIG. 1B is a top-down (plan) view of system 101 for MRI guided breast intervention, according to some embodiments of the present invention.

FIG. 1C is a top-down view of tissue-compression fixture 120 for MRI guided breast intervention, according to some embodiments of the present invention.

FIG. 1D is a top-down view of tissue-compression fixture 120 for MRI guided breast intervention, according to some embodiments of the present invention.

FIG. 2A is a perspective view of a tissue-stabilization device 140 having a tissue-compression cradle 200, according to some embodiments of the present invention.

FIG. 2B is a perspective view of tissue-compression cradle 200 in a relatively open and uncompressed configuration.

FIG. 2C is a perspective view of tissue-compression cradle 200 in a relatively snug compressed configuration.

FIG. 5C-2 is a perspective schematic view of a breast-compression cradle 503 having a plurality of tissue-compression members 593, wherein cradle 503 is in an open configuration.

DESCRIPTION OF PREFERRED EMBODIMENTS

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Figure 1A:
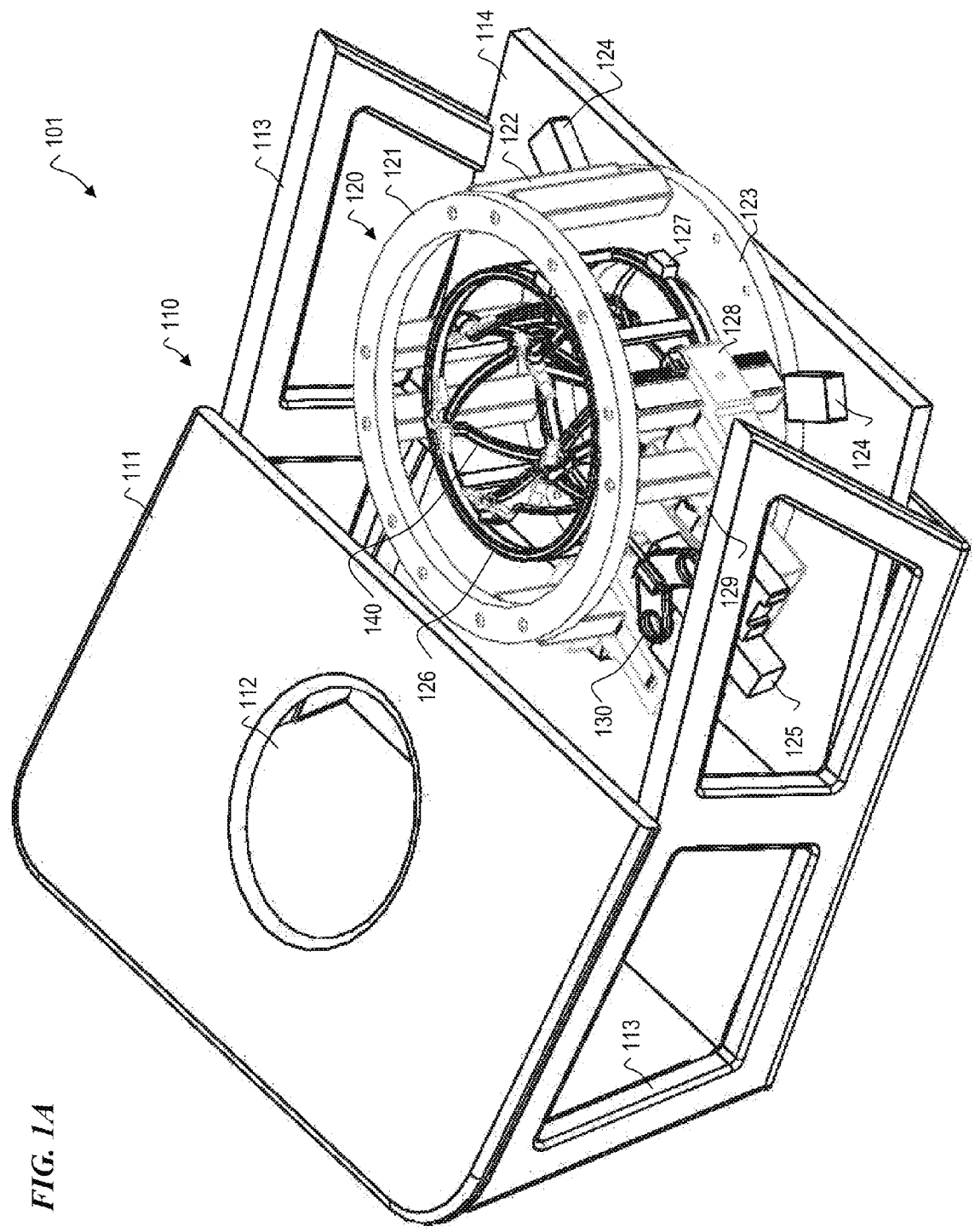
FIG. 1A is a perspective view of system 101 for MRI-guided breast intervention, according to some embodiments of the present invention.

FIG. 1A is a perspective view of MRI-guided breast intervention system 101, according to some embodiments of the present invention. In some embodiments, system 101 includes support structure 110 that includes frame base 114, two outside-support side frames 113 arranged on the sides of support structure 110, and at least a first patient-support surface 111 arranged on and supported by the outside-support frames 113. In some embodiments, each patient-support surface 111 includes a breast opening 112 to accommodate a breast of a patient during the MRI-guided breast intervention to provide improved patient support and/or comfort. In some embodiments, system 101 includes a second patient-support surface (not shown) that is arranged over tissue-compression-and-biopsy fixture 120, is supported by outside-support frame 113 and is substantially a mirror image of patient-support surface 111. During an MRI-guided breast intervention, a breast of a patient that is to receive an intervention is lowered (e.g., by gravity) through a breast opening 112 in the second patient-support surface (not shown) and into tissue-compression-and-biopsy fixture 120 for the intervention procedure.

In some embodiments, tissue-compression-and-biopsy fixture 120 includes rotating-base plate 123 arranged on frame base 114, a plurality of support members 122 arranged circumferentially around the rotating-base plate 123, outer-rotating ring 121 arranged on and supported by the plurality of support members 122, a plurality of outer-ring rotary actuators 124 located on frame base 114 and arranged circumferentially around rotating-base plate 123 to selectively rotate it relative to other structures on frame 110. In some embodiments, breast-compression cradle 140 is supported by base 114 and is separate from inner-rotating ring 126 (such that inner ring 126 and interconnected outer ring members 121-122-123 can be independently rotated around breast-compression cradle 140, in order to perform various procedures without moving a patient 99 (not shown here) or her breast). In some embodiments, breast-compression cradle 140 is positioned within an opening in the outer ring members 121 and 122 that are affixed to rotating-base plate 123. In some embodiments, a plurality of inner-ring rotary actuators 127 are located on rotating-base plate 123 and arranged circumferentially around the outer perimeter of inner-rotating ring 126 and configured to rotate it around a center axis of breast-compression cradle 140. An intervention probe 130 is replaceably attached to probe actuator 125 (via an attachment (probe-receptacle) mechanism 131 such as shown in FIG. 1B) and arranged to travel radially (or at an acute angle to a radius of the cylindrical opening) inward and outward with respect to the breast-compression cradle 140. In some embodiments, probe actuator 125 is attached to one or more outer-elevator actuators 128 and to one or more inner-elevator actuators 129. The intervention probe 130 is arranged on the inner-elevator actuators 129 and the outer-elevator actuators 128 such that the intervention probe 130 travels up and down in a Z-direction (i.e., in the direction perpendicular with respect to the frame base 114 as shown in FIG. 1A) when the inner-elevator actuator(s) 129 and the outer-elevator actuator(s) 128 travel together in the same distance and in the same direction. The angle the intervention probe 130 makes with the plane of the frame base 114 is increased or decreased by operating the inner-elevator actuators 129 and the outer-elevator actuators 128 by different distances in the same direction or by suitable amounts in opposite directions (e.g., assuming the initial position of the intervention probe 130 is set to be parallel to the plane of the frame base, the angle between the intervention probe 130 and the frame base 114 is increased when the outer-elevator actuators travel in a positive Z-direction and the inner-elevator actuators travel in a negative Z-direction).

In some embodiments, the parts and components of MRI-guided breast-intervention system 101 are selected such that they are compatible with an MRI machine (i.e, the MRI-guided breast-intervention system 101 is capable of being used within the MRI machine while the MRI machine is in an operating state). In some such embodiments, the materials used for fabricating these parts are polymers or materials such as nitinol.

FIG. 1B is a top-down view of MRI-guided breast-intervention system 101, according to some embodiments of the present invention. In some embodiments, the numbered elements of FIG. 1B are the same as or equivalent to the corresponding elements described above for FIG. 1A. FIG. 1B also includes some features not shown or explicitly identified in FIG. 1A. In some embodiments, intervention probe 130 further includes probe receptacle 131 attached to intervention probe 130 and configured to replaceably accept and hold a plurality of interchangeable probe tips 132. In some embodiments, probe receptacle 131 is configured to automatically detach a first probe tip from the intervention probe 130 into a receptacle and then attach a second probe tip. In some embodiments, probe tip 132 is a fine needle used to take a biopsy sample from a lesion in a breast 98 of a patient 99 (see FIG. 2A). In some embodiments, probe receptacle 131 is configured to accept a plurality of probe tips simultaneously.

FIG. 1C and FIG. 1D are top-down views of tissue-compression-and-biopsy fixture 120 for MRI-guided breast intervention, according to some embodiments of the present invention. In some embodiments, the numbered elements of FIG. 1C and FIG. 1D are the same as or equivalent to the corresponding elements described above for FIG. 1A and FIG. 1B. In some embodiments, arrow 81 of FIG. 1C is used to depict the rotation of rotating-base plate 123 in a counter-clockwise direction (as shown in FIG. 1C) relative to inner-rotating ring 126 (e.g., keeping inner-rotating ring 126 stationary) such that probe tip 132 is rotated to the left (counterclockwise relative to a central pivot point) as compared to the position of intervention probe 130 in FIG. 1B. In some embodiments, arrow 82 of FIG. 1D depicts the rotation of inner-rotating ring 126 in a counterclockwise direction (as shown in FIG. 1D) relative to outer-rotating ring 123 (e.g., keeping rotating-base plate 123 stationary) such that probe tip 132 is rotated to the right (clockwise relative to a central pivot point) as compared to the position of intervention probe 130 in FIG. 1C.

Figure 1E:
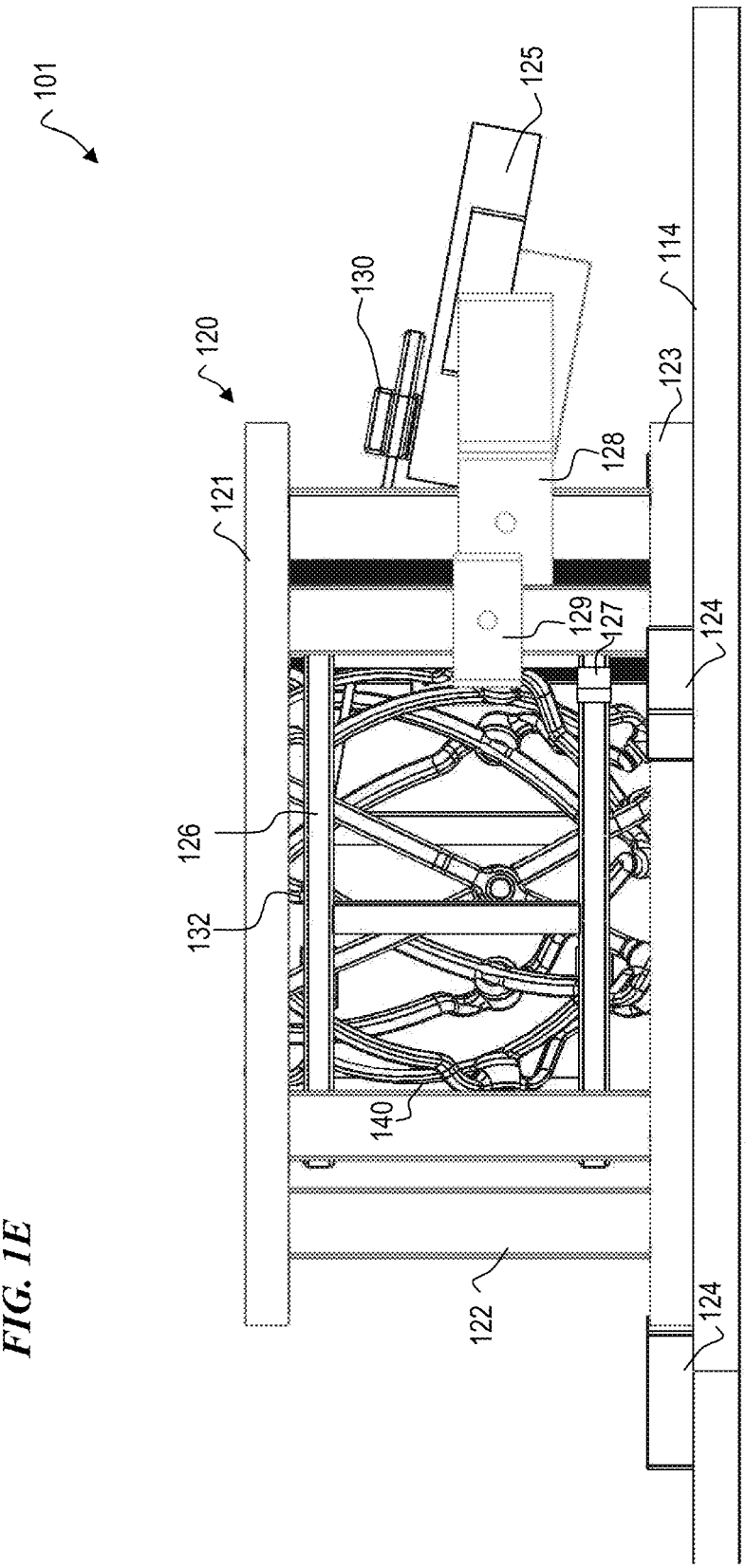
FIG. 1E is a side (elevational) view of system 101 for MRI guided breast intervention, according to some embodiments of the present invention.
Figure 1F:
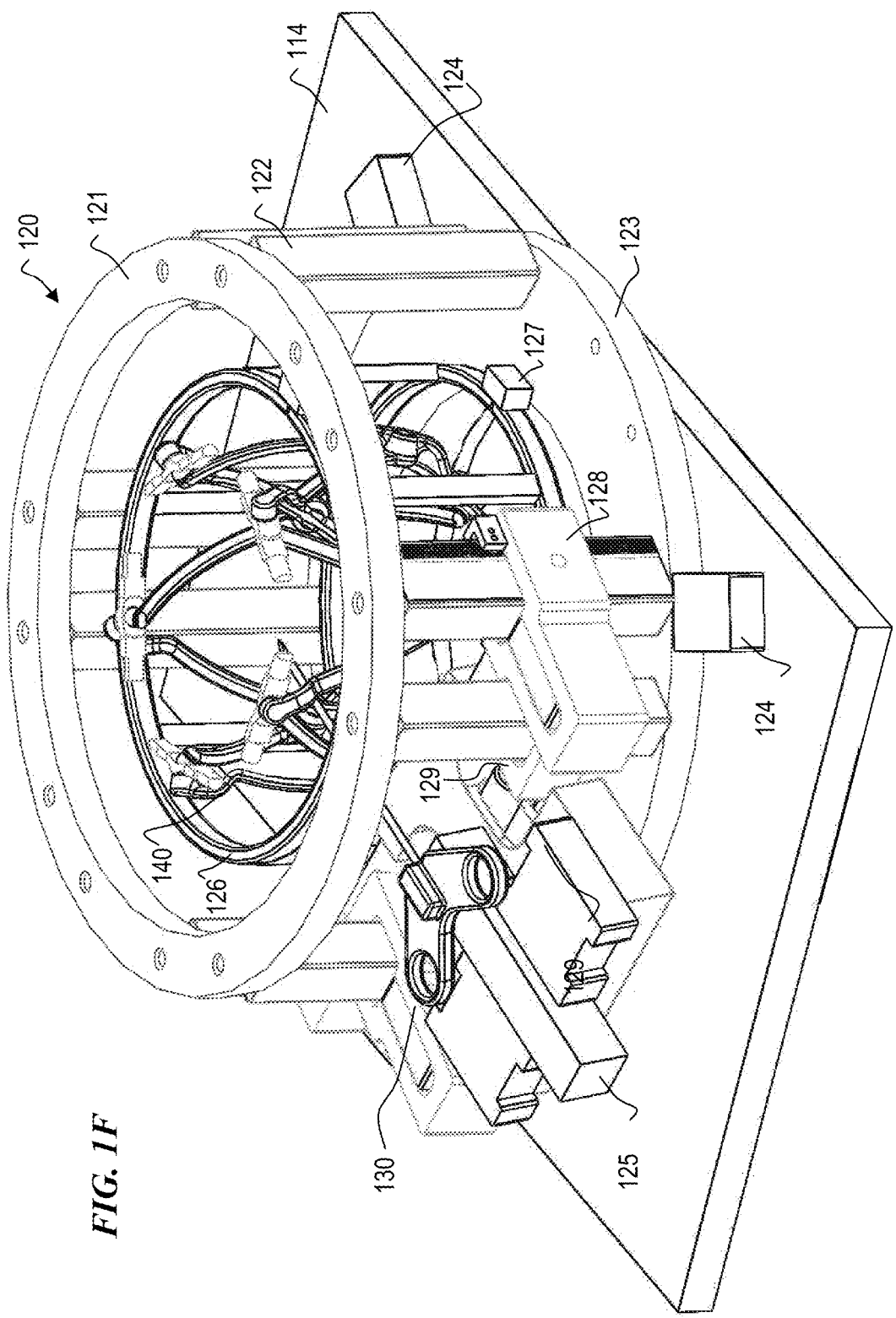
FIG. 1F is a perspective view of tissue-compression fixture 120 for MRI guided breast intervention, according to some embodiments of the present invention.

FIG. 1E is a side view of MRI-guided breast-intervention system 101 and FIG. 1F is a perspective view of tissue compression and biopsy fixture 120 for MRI-guided breast intervention, according to some embodiments of the present invention. In some embodiments, the numbered elements of FIG. 1E and FIG. 1F are the same as or equivalent to the corresponding elements described above for FIG. 1A and FIG. 1B. In some embodiments, FIG. 1E and FIG. 1F are two views of system 101 that show intervention probe 130 in an angled-up position, wherein the outer-elevator actuators 128 have been moved in an upward z-direction and the inner-elevator actuators 129 have been moved in a downward z-direction such that the angle between the intervention probe 130 and the frame base has increased.

FIG. 2A is a perspective side view of a tissue-compression device 140, according to one embodiment of the present invention. In some embodiments, compression device 140 includes a pantomesh breast-compression cradle 200 that has a plurality of pairs of links (each such pair called a "pantomesh element" herein), each pair (pantomesh element) including a first link 211 and a second link 212, wherein each link has a first end (e.g., the upper end in the FIG. 1A) and a second end (e.g., the lower end in the FIG. 2A). Each pair of links includes a first link and a second link, and wherein the plurality of pairs of links includes a first pair 210 and a second pair 210; a plurality of revolute joints, including a first revolute joint 213 and a second revolute joint 213, wherein the first revolute joint 213 connects a location between the first end and the second end of the first link 211 of the first pair 210 to a location between the first end and the second end of the second link 212 of the first pair 210, and the second revolute joint 213 connects a location between the first end and the second end of the first link 211 of the second pair 210 to a location between the first end and the second end of the second link 212 of the second pair 210; and a plurality of spherical joints that includes a first spherical joint 216 and a second spherical joint 219, wherein the first spherical joint 216 connects the first end of the first link 211 of the first pair of links 210 to the first end of the second link 212 of the second pair of links 210, and the second spherical joint 219 connects the second end of the second link 212 of the first pair of links 210 to the second end of the first link 211 of the second pair of links 210.

In some embodiments, the present invention provides a second apparatus that includes a pantomesh that includes: a first plurality of pantomesh elements including a first pantomesh element, a second pantomesh element and an $N^{th}$ pantomesh element, where N is an integer larger than 2, and wherein each one of the first plurality of pantomesh elements includes: a pair of links including a first link and a second link, wherein each link of the pair of links has a first end and a second end; a revolute joint wherein the revolute joint connects a location between the first end and the second end of the first link to a location between the first end and the second end of the second link; and a plurality of spherical joints that includes a first spherical joint, a second spherical joint, a third spherical joint, and a fourth spherical joint, wherein the first spherical joint is attached to the first end of the first link, the second spherical joint is attached to the second end of the first link, the third spherical joint is attached to the first end of the second link, and the fourth spherical joint is attached to the second end of the second link, wherein the first and third spherical joints of the first pantomesh element connect to the second and fourth spherical joints, respectively, of the second pantomesh element of a first row of the first plurality of pantomesh elements, and the second and fourth spherical joints of the first pantomesh element connect to the first and third spherical joints, respectively, of the $N^{th}$ pantomesh element of the first row, and wherein a first line that extends through the first spherical joint and the third spherical joint of the first pantomesh element forms a first variable angle with a second line that extends through the second spherical joint and the fourth spherical joint of the first pantomesh element, and wherein the first variable angle changes as a distance between the first and third spherical joints increases.

In some embodiments, breast-compression fixture 140 that includes an outer frame 220, a plurality of actuators including a first actuator 227 and a second actuator 229. The breast-compression fixture 140 includes a breast-compression cradle 200, including a plurality of pantomesh elements 210 (in some embodiments, one or more rows of pantomesh elements are connected to one another to form a closed ring (also called a closed pantomesh)), each pantomesh element 210 having two compression members 211 and 212. When in use as an aid to a breast-intervention medical procedure, the chest wall 97 of the patient 99 rests on the breast-compression fixture 140 (or on a platform (not shown here) located just above fixture 140) such that the breast 98 hangs down due to gravity and is surrounded by the closed pantomesh that includes compression members 211 and 212.

In some embodiments of this invention, the closed pantomesh includes four pantomesh elements 210, wherein each pantomesh element 210 includes a pair of links, wherein the pair of links includes a first link 211 and a second link 212, wherein each link has a first end (e.g., the lower ends in FIG. 2A) and a second end (e.g., the upper ends in FIG. 2A). Each pantomesh element 210 also includes a revolute joint 213 that connects a location between the first end and the second end of the first link 211 of the pantomesh element 210 to a location between the first end and the second end of the second link 212 of the pantomesh element 210; and a plurality of spherical joints that includes a first spherical joint 216, second spherical joint 217, spherical third spherical joint 218, and a fourth spherical joint 219. The first spherical joint 216 connects the first end of the first link 211 of the first pantomesh element 210 (e.g., the pantomesh element seen in the center of FIG. 2A); to the first end of the second link of a second pantomesh element 210 (e.g., the pantomesh element seen end-on at the right of FIG. 2A); the second spherical joint 217 connects the second end of the first link 211 of the first pantomesh element to the second end of the second link of the third pantomesh element 210 (e.g., the pantomesh element seen edge-on at the left of FIG. 2A); the third spherical joint 218 connects the first end of the second link 212 of the first pantomesh element to the first end of the first link of the third pantomesh element; and the fourth spherical joint 219 connects the second end of the second link 212 of the first pantomesh element to the second end of the first link of the second pantomesh element. In a similar manner, if four pantomesh elements are implemented, spherical joints connect corresponding links of the second, third and fourth pantomesh elements, not fully visible in FIG. 2A. In other embodiments, this invention includes a plurality of a different number of pantomesh elements, where the number is not equal to four.

FIG. 2B shows the breast-compression cradle 200, also shown in FIG. 2A, in an expanded relatively open and uncompressed configuration. In this view, the ring 220 and actuators 227 and 229 are not shown. To achieve this configuration, the actuators 227 and 229 would pull each of a plurality of the spherical joints 227 and 229 in an outward direction (e.g., in some embodiments, in a radially outward direction from a virtual centerline of the breast 98 that extends outward from the patient through a central (e.g., vertical in this view) axis of cradle 200.

FIG. 2C is an isometric view of the breast-compression cradle 200, also shown in FIG. 2A, in a relatively snug compressed configuration. In this view, the ring 220 and actuators 227 and 229 are not shown. To achieve this configuration, the actuators 227 and 229 would push each of a plurality of the spherical joints 227 and 229 in an inward direction (e.g., in some embodiments, in a radially inward direction toward a virtual centerline of the breast 98 that extends outward from the patient through a central (e.g., vertical in this view) axis of cradle 200.

When actuated to such a compressed state, the breast is stabilized and can be probed without releasing and recompressing, as was done in conventional MRI biopsy machines. One purpose of the device is to position a probe, such as a biopsy needle 132 (see FIG. 1B), in a breast 98 that is held by a stabilization device such as 200. The rotary degree of freedom (DOF) actuator unit 124 (as used herein, such an actuator is also called a DOF unit or simply a DOF, where the meaning will be readily apparent from the context) rotates relative to the base 114 and around the breast 98. Two heights, the inside height set by actuator 129 and the outside height set by actuator 128, together determine the height and elevational/declination angle of the probe 130. A translational or rotational DOF actuator 127 (e.g., in some embodiments, a linear actuator, while in other embodiments, a rotational actuator) moves the probe laterally compared to the rotary axis. The needle is finally delivered to the target by using the insertion DOF 125 (e.g., in some embodiments, a linear actuator).

Figure 3A:
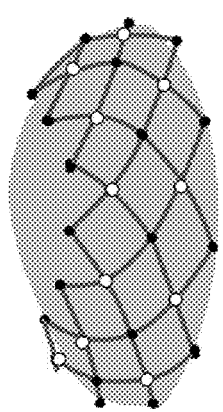
FIG. 3A is a perspective view of a multiple-row closed-pantomesh tissue-stabilization device 340 (in a first uncompressed state) that is used for tissue-compression cradle 200, according to some embodiments of the present invention.

FIG. 3A is a perspective view of a multiple-row closed-pantomesh tissue-stabilization device 340 (in a first uncompressed state) that is used for tissue-compression cradle 200, according to some embodiments of the present invention.

Figure 3B:
FIG. 3B is a perspective view of a multiple-row closed-pantomesh tissue-stabilization device 340 (in a second partially compressed state) that is used for tissue-compression cradle 200, according to some embodiments of the present invention.

FIG. 3B is a perspective view of a multiple-row closed-pantomesh tissue-stabilization device 340 (in a second partially compressed state) that is used for tissue-compression cradle 200, according to some embodiments of the present invention.

Figure 3C:
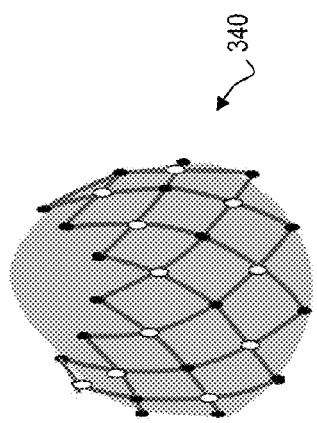
FIG. 3C is a perspective view of a multiple-row closed-pantomesh tissue-stabilization device 340 (in a third more compressed state) that is used for tissue-compression cradle 200, according to some embodiments of the present invention.

FIG. 3C is a perspective view of a multiple-row closed-pantomesh tissue-stabilization device 340 (in a third more compressed state) that is used for tissue-compression cradle 200, according to some embodiments of the present invention.

Figure 4:
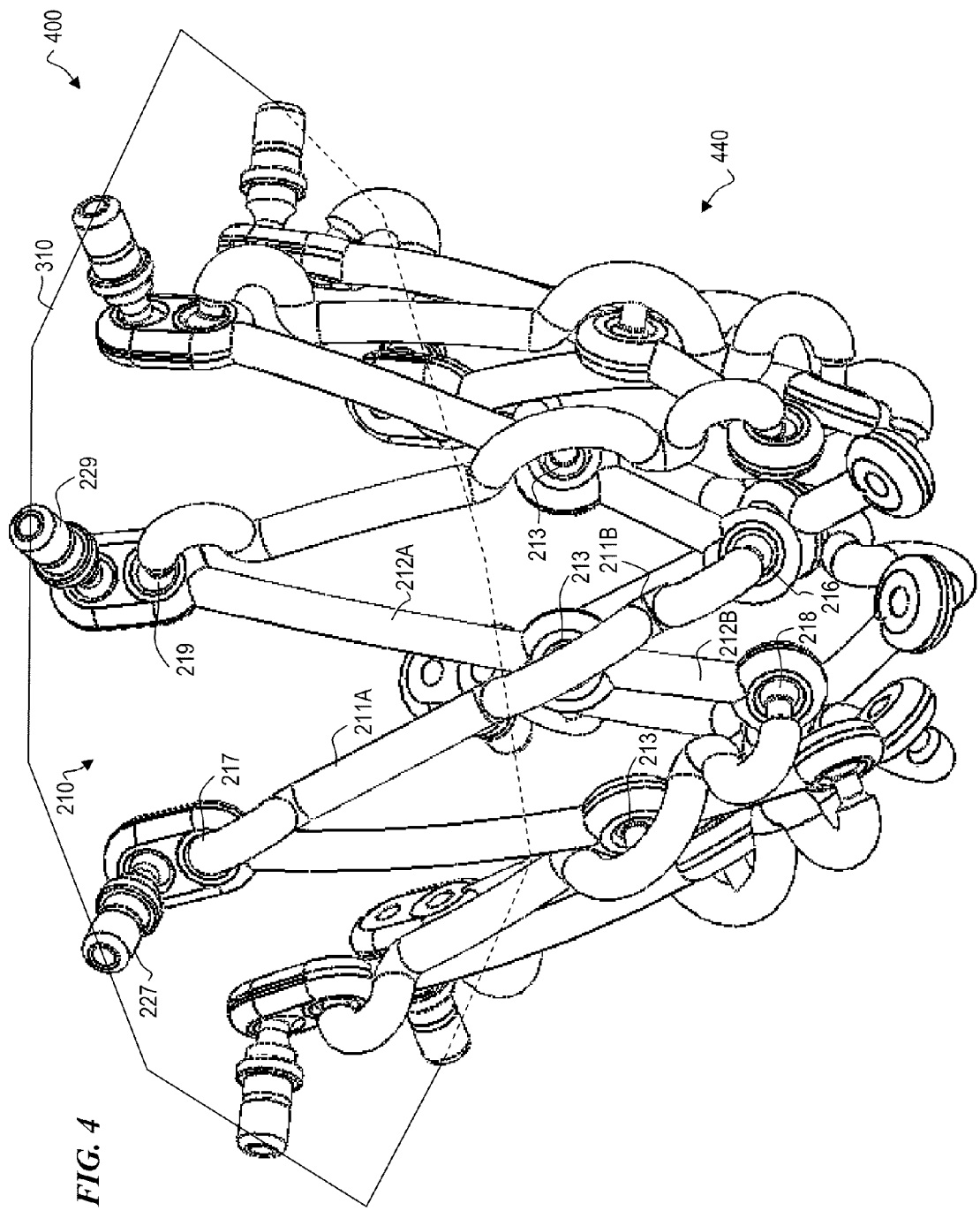
FIG. 4 is a perspective view of a single-row closed-pantomesh tissue-stabilization device 440 that is used for tissue-compression cradle 200, according to some embodiments of the present invention.

FIG. 4 is a perspective view of a single-row closed-pantomesh tissue-stabilization device 440 that is used for tissue-compression cradle 400, according to some embodiments of the present invention. In the embodiment shown, tissue-stabilization device 440 includes eight pantomesh elements 210, each having elements corresponding to like-numbered elements of FIG. 2A described in detail above.

Figure 5A:
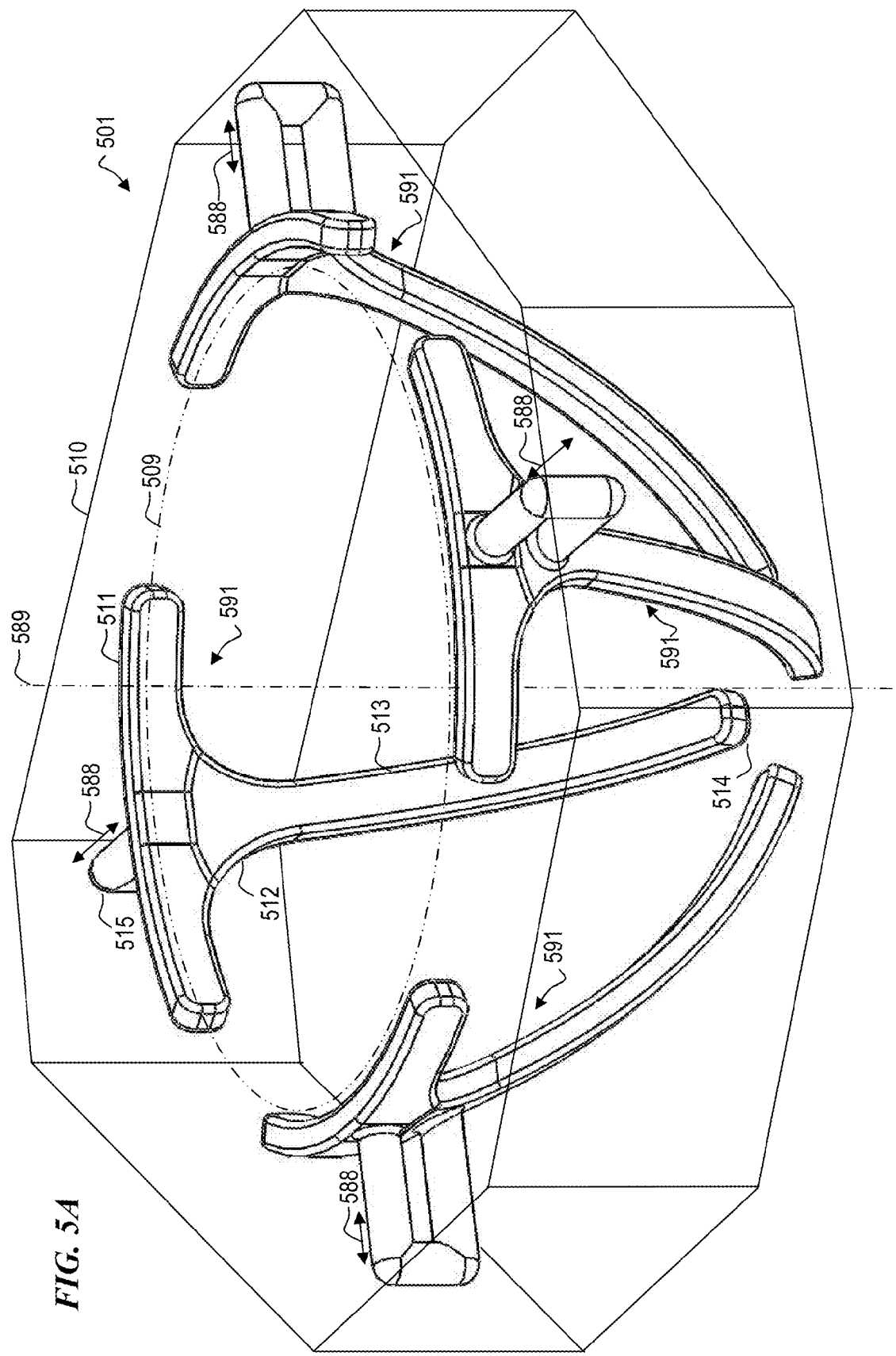
FIG. 5A is a perspective schematic view of a breast-compression cradle 501 having a plurality of tissue-compression members 591.

FIG. 5A is a perspective schematic view of a breast-compression cradle 501 having a plurality of tissue-compression members 591 (in the embodiment shown, four tissue-compression members 591 are used, while in other embodiments, other numbers of tissue-compression members 591 are used). In some embodiments, cradle 501 includes a plurality of three or more tissue-compression members 591 that are configured to be moved to compress bodily tissue of a portion of a patient (e.g., a breast). In some embodiments, breast-compression cradle 501 captures and compresses the patient's breast as the breast hangs down from the patient (due to gravity) when the patient is lying in a prone (face-down) position. In some embodiments, the plurality of tissue-compression members 591 are interconnected to one another via respective connections to cradle fixture 510, and cradle 501 compresses the patient's breast by moving the plurality of tissue-compression members 591 radially inward along a direction indicated by line 588 (away from the perimeter of cradle fixture 510 and toward a center line 589 that runs vertically through cradle 501). When the plurality of tissue-compression members 591 are moved radially outward, compression is removed and the breast is released. In some embodiments, tissue-compression members 591 are moved radially inward and outward along directions indicated by the respective lines 588 by actuators (in some embodiments, for example, piezoelectric actuators, not shown here) connected to tissue-compression members 591 via an actuator connection 515. In some embodiments, actuator connection 515 is a closed shape (e.g., approximately C-shaped), and each actuator connection 515 is connected to, and moved by a single actuator. In some embodiments, each actuator is independently moveable under computer control.

In some embodiments, each one of the plurality of tissue-compression members 591 includes a circumferential element 511 that curves around at least a portion of a circumference 509 formed by the plurality of tissue-compression members 591. In some embodiments, one or more of the tissue-compression members 591 can also be moved up and down in order to better conform to the patient's rib cage (e.g., in some such embodiments, one can be moved upward under the arm of the patient to better compress and obtain MRI images of breast and lymph tissue there). In some embodiments, one or more of the circumferential elements 511 is springy and/or pliable, in order to provide comfort and/or a snugger fit. In some embodiments, actuator connection 515 connects to circumferential element 511 such that circumferential element 511 moves radially inward during compression. In some embodiments, each one of the plurality of tissue-compression members 591 includes a stem-shaped compression element 513 that includes an upper end 512 (attached to a respective circumferential element 511) and a free lower end 514. In some embodiments, one or more of the stem elements 513 is springy and/or pliable, in order to provide comfort and/or a snugger fit. In some embodiments, each stem 513 has a curved configuration such that when cradle 501 is in a compressed state (as illustrated in FIG. 5A), the lower end 514 of stem 513 is closer to center line 589 than the upper end 512 of stem 513. In some embodiments, stem 513 connects to its corresponding circumferential element 511 at the center of circumferential element 511 such that tissue-compression member 591 forms a T-shape (as illustrated in FIG. 5A). In other embodiments (not shown), stem 513 connects to its corresponding circumferential element 511 at one end of circumferential element 511 such that tissue-compression member 591 forms an inverted L-shape, or connects to its corresponding circumferential element 511 at some other suitable location (e.g., between the center and the end) of circumferential element 511.

In some embodiments, each one of the plurality of tissue-compression members 591 is made of a magnetic-resonance imaging (MRI)-safe material (e.g., nitinol or polymer or other compatible material). In some embodiments, tissue-compression members 591 include embedded MRI coils or coil portions, or have such coil portions attached to them.

Figure 5B:
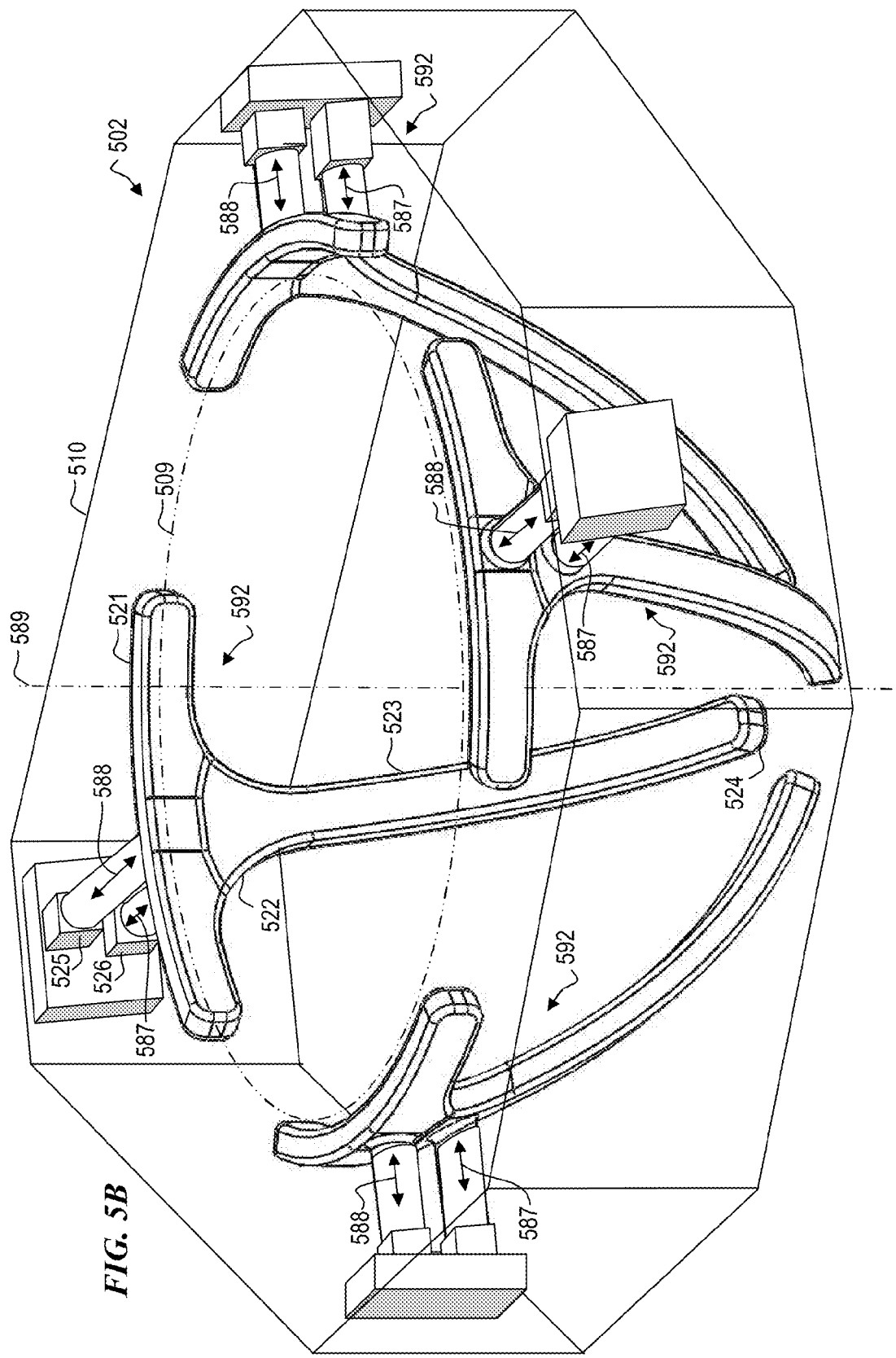
FIG. 5B is a perspective schematic view of a breast-compression cradle 502 having a plurality of tissue-compression members 592.

FIG. 5B is a perspective schematic view of a breast-compression cradle 502 having a plurality of tissue-compression members 592 (in the embodiment shown, four tissue-compression members 592 are used, while in other embodiments, other numbers of tissue-compression members 592 are used). In some embodiments, each one of the plurality of tissue-compression members 592 includes a circumferential element 521 that curves around at least a portion of a circumference 509 formed by the plurality of tissue-compression members 592. In some embodiments, one or more of the tissue-compression members 592 can also be moved up and down in order to better conform to the patient's rib cage (e.g., in some such embodiments, one can be moved upward under the arm of the patient to better compress and obtain MRI images of breast and lymph tissue there). In some embodiments, one or more of the circumferential elements 521 is springy and/or pliable, in order to provide comfort and/or a snugger fit. In some embodiments, each one of the plurality of tissue-compression members 592 includes a stem-shaped compression element 523 that includes an upper end 522 (attached to a respective circumferential element 521) and a free lower end 524. In some embodiments, each stem 523 has a curved configuration such that when cradle 502 is in a compressed state (as illustrated in FIG. 5B), the lower end 524 of stem 523 is closer to center line 589 than the upper end 522 of stem 523. In some embodiments, stem 523 connects to its corresponding circumferential element 521 at the center of circumferential element 521 such that tissue-compression member 592 forms a T-shape (as illustrated in FIG. 5B). In other embodiments (not shown), stem 523 connects to its corresponding circumferential element 521 at one end of circumferential element 521 such that tissue-compression member 592 forms an inverted L-shape, or connects to its corresponding circumferential element 521 at some other suitable location (e.g., between the center and the end) of circumferential element 521.

In some embodiments, at least one of the plurality of tissue-compression members 592 includes two actuators (in some embodiments, for example, piezoelectric actuators). In some embodiments, for example, at least one of the plurality of tissue-compression members 592 includes an upper actuator 525 and a lower actuator 526. In some embodiments, upper actuator 525 is configured to move radially inward and outward along a direction indicated by line 588 such that circumferential element 521 moves radially inward and outward. In some embodiments, lower actuator 526 is configured to move radially inward and outward along a direction indicated by line 587 such that stem 523 can be tilted relative to circumferential element 521.

In some embodiments, each one of the plurality of tissue-compression members 592 is made of a magnetic-resonance imaging (MRI)-safe material (e.g., nitinol or polymer or other compatible material). In some embodiments, tissue-compression members 592 include embedded MRI coils or coil portions, or have such coil portions attached to them.

Figures 1, 5C:
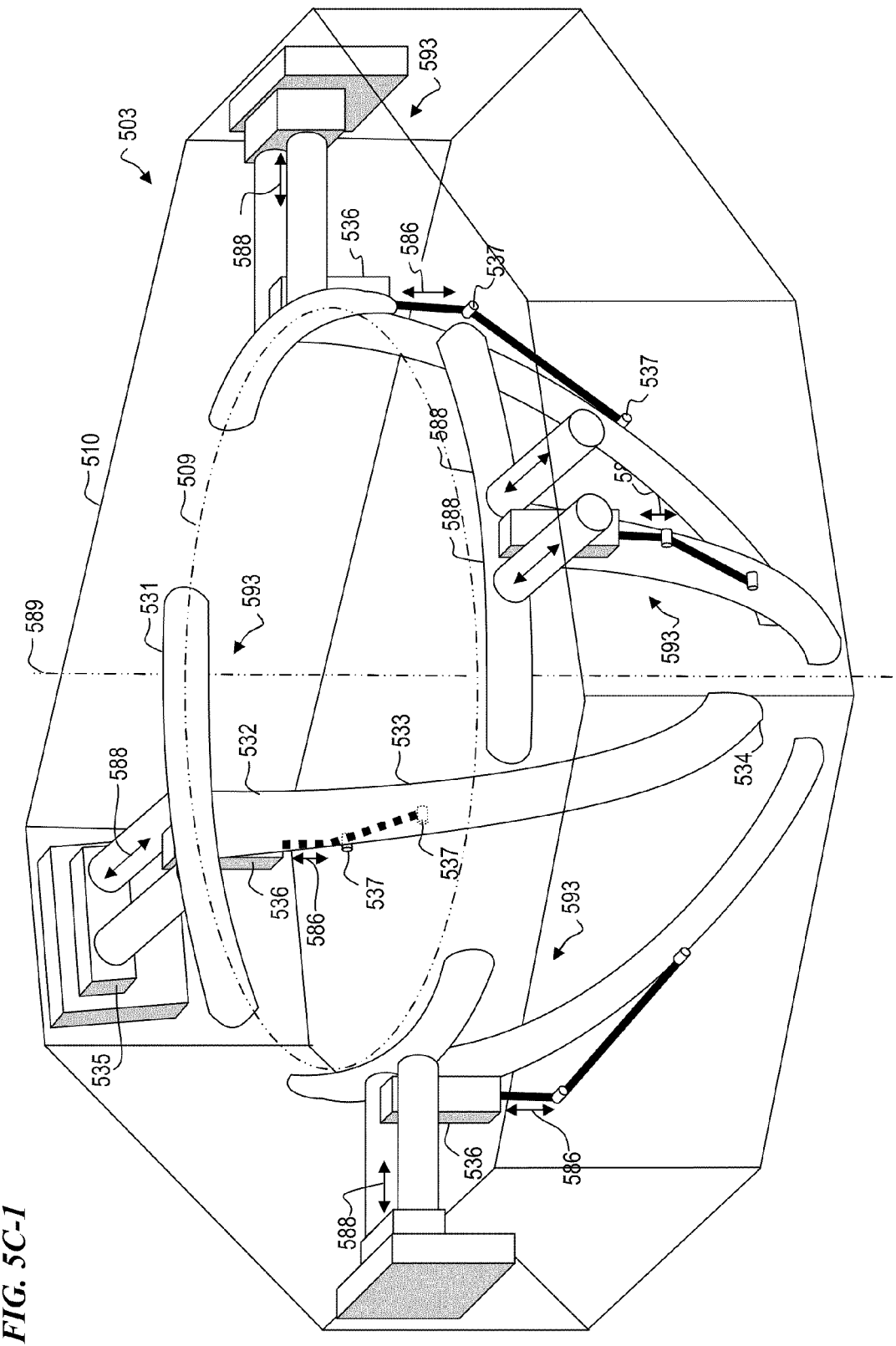
FIG. 5C-1 is a perspective schematic view of a breast-compression cradle 503 having a plurality of tissue-compression members 593, wherein cradle 503 is in a compressed configuration.
Figures 2, 5C:
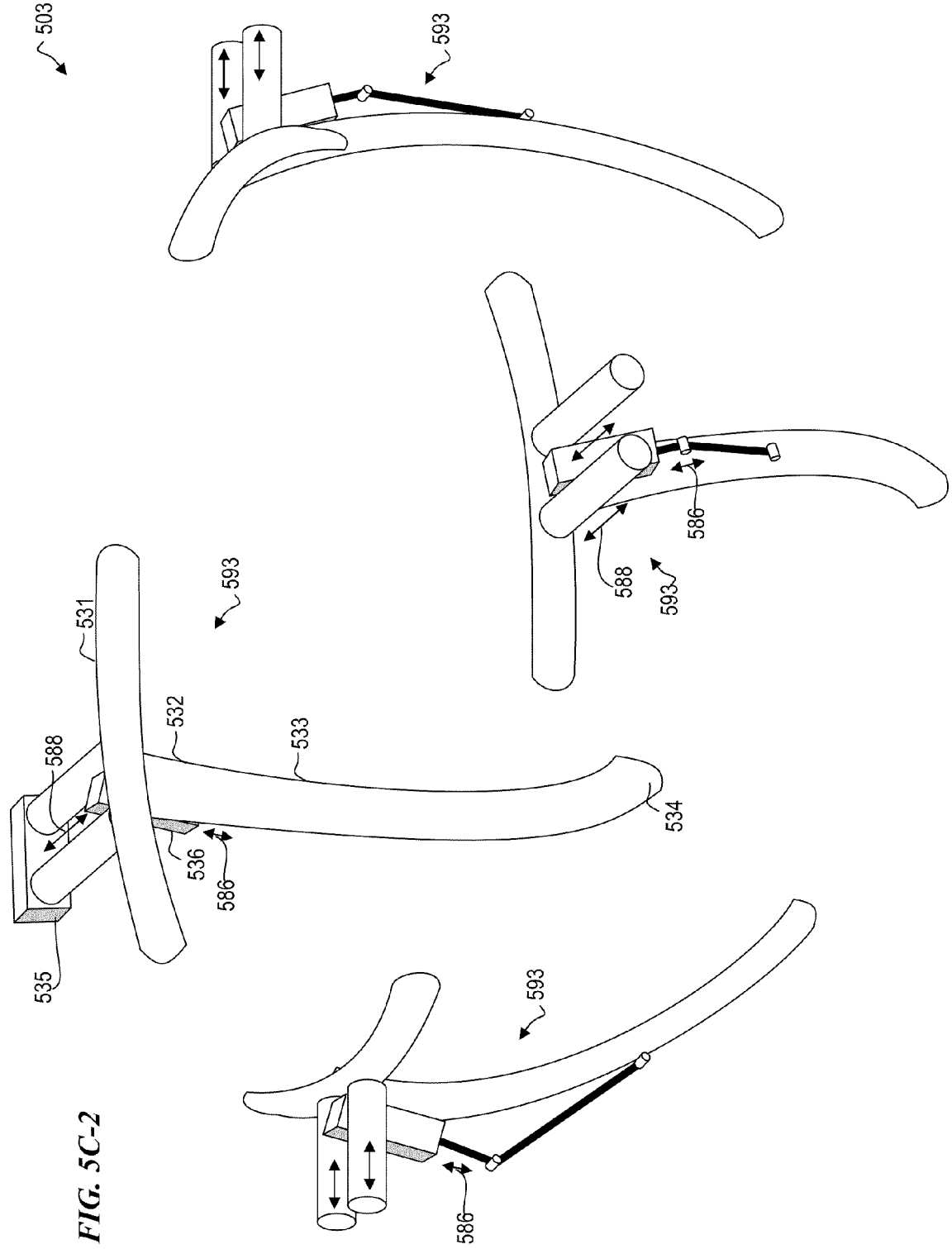

FIG. 5C-1 is a perspective schematic view of a breast-compression cradle 503 having a plurality of tissue-compression members 593 (in the embodiment shown, four tissue-compression members 593 are used, while in other embodiments, other numbers of tissue-compression members 593 are used). In some embodiments, each one of the plurality of tissue-compression members 593 includes a circumferential element 531 that curves around at least a portion of a circumference 509 formed by the plurality of tissue-compression members 593. In some embodiments, one or more of the tissue-compression members 593 can also be moved up and down in order to better conform to the patient's rib cage (e.g., in some such embodiments, one can be moved upward under the arm of the patient to better compress and obtain MRI images of breast and lymph tissue there). In some embodiments, one or more of the circumferential elements 531 is springy and/or pliable, in order to provide comfort and/or a snugger fit. In some embodiments, each one of the plurality of tissue-compression members 593 includes a stem-shaped compression element 533 that includes an upper end 532 (attached to a respective circumferential element 531) and a free lower end 534. In some embodiments, one or more of the stem elements 533 is springy and/or pliable, in order to provide comfort and/or a snugger fit. In some embodiments, stem 533 has a curved configuration such that when cradle 503 is in a compressed state (as illustrated in FIG. 5C-1), the lower end 534 of stem 533 is closer to center line 589 than the upper end 532 of stem 533. In some embodiments, stem 533 connects to its corresponding circumferential element 531 at the center of circumferential element 531 such that tissue-compression member 593 forms a T-shape (as illustrated in FIGS. 5C-1 and 5C-2). In other embodiments (not shown), stem 533 connects to its corresponding circumferential element 531 at one end of circumferential element 531 such that tissue-compression member 593 forms an inverted L-shape, or connects to its corresponding circumferential element 531 at some other suitable location (e.g., between the center and the end) of circumferential element 531.

In some embodiments, at least one of the plurality of tissue-compression members 593 includes two actuators (in some embodiments, for example, piezoelectric actuators). In some embodiments, for example, at least one of the plurality of tissue-compression members 593 includes a first actuator 535 and a second actuator 536. In some embodiments, first actuator 535 is configured to move radially inward and outward along a direction indicated by line 588 such that circumferential element 531 moves radially inward and outward. In some embodiments, second actuator 536 includes a hinged mechanism 537 that connects actuator 536 to stem 533, and actuator 536 is configured to move vertically up and down along a direction indicated by line 586 such that stem 533 can be tilted relative to circumferential element 531. FIG. 5C-1 illustrates a compressed configuration of cradle 503, wherein actuator 525 is moved radially inward (toward center line 589) such that circumferential element 531 is moved radially inward toward center line 589 and actuator 536 is moved vertically downward such that stem 533 is tilted in toward center line 589. FIG. 5C-2 illustrates an open configuration of cradle 503, wherein actuator 525 is moved radially outward (away from center line 589) and actuator 536 is moved vertically upward such that circumferential element 531 and stem 533 are both moved radially outward from center line 589.

In some embodiments, each one of the plurality of tissue-compression members 593 are made of a magnetic-resonance imaging (MRI)-safe material (e.g., nitinol or polymer or other compatible material). In some embodiments, tissue-compression members 593 include embedded MRI coils or coil portions, or have such coil portions attached to them.

Figure 5D:
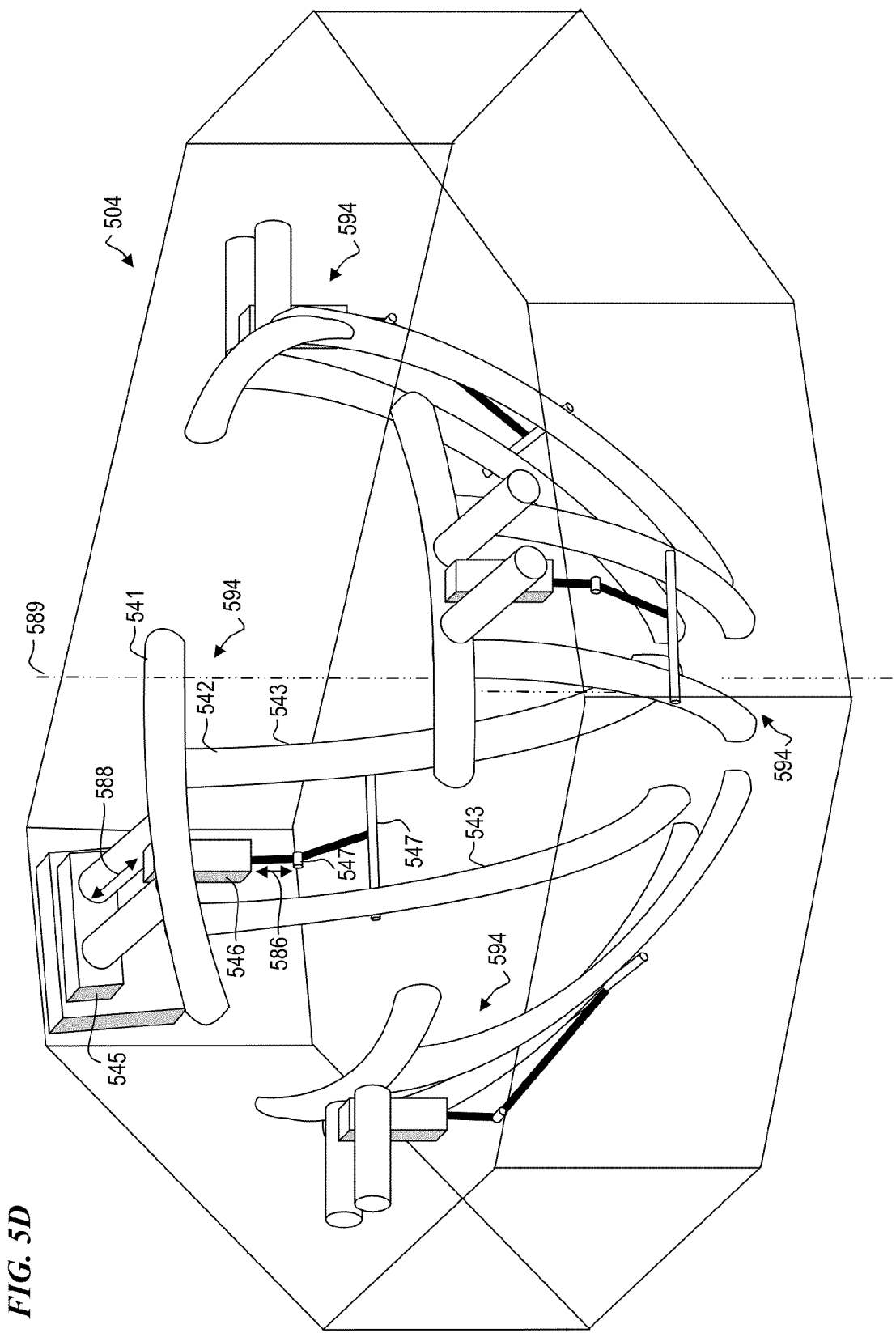
FIG. 5D is a perspective schematic view of a breast-compression cradle 504 having a plurality of tissue-compression members 594.

FIG. 5D is a perspective schematic view of a breast-compression cradle 504 having a plurality of tissue-compression members 594 (in the embodiment shown, four tissue-compression members 594 are used, while in other embodiments, other numbers of tissue-compression members 594 are used). In some embodiments, each one of the plurality of tissue-compression members 594 includes a circumferential element 541 that curves around at least a portion of a circumference 509 formed by the plurality of tissue-compression members 594. In some embodiments, one or more of the tissue-compression members 594 can also be moved up and down in order to better conform to the patient's rib cage (e.g., in some such embodiments, one can be moved upward under the arm of the patient to better compress and obtain MRI images of breast and lymph tissue there). In some embodiments, one or more of the circumferential elements 541 is springy and/or pliable, in order to provide comfort and/or a snugger fit.

In some embodiments, each one of the plurality of tissue-compression members 594 includes two or more stem-shaped compression elements 543, wherein each one of the two or more stems 543 includes an upper end 542 (attached to a respective circumferential element 541) and a free lower end 544. In some embodiments, one or more of the stem elements 543 is springy and/or pliable, in order to provide comfort and/or a snugger fit. In some embodiments, the two or more stems 543 connect to circumferential element 541 in an evenly-distributed manner (e.g., in some embodiments, as illustrated in FIG. 5D, tissue-compression member 594 includes a first stem 543 and a second stem 543, wherein first stem 543 is connected to circumferential element 541 at a location on the left side of circumferential element 541, wherein second stem 543 is connected to circumferential element 541 at a location on the right side of circumferential element 541, and wherein first stem 543 and second stem 543 are equidistant from the center of circumferential element 541). In other embodiments (not shown), the two or more stems 543 are connected to circumferential element 541 in some other suitable manner (e.g., both stems 543 are located on one side of circumferential element 541).

In some embodiments, stems 543 have a curved configuration such that when cradle 504 is in a compressed state (as illustrated in FIG. 5D), the lower end 544 of stems 543 is closer to center line 589 than the upper end 542 of stems 543. In some embodiments, at least one of the plurality of tissue-compression members 594 includes two actuators (in some embodiments, for example, piezoelectric actuators). In some embodiments, for example, at least one of the plurality of tissue-compression members 594 includes a first actuator 545 and a second actuator 546. In some embodiments, first actuator 545 is configured to move radially inward and outward along a direction indicated by line 588 such that circumferential element 541 moves radially inward and outward. In some embodiments, second actuator 546 includes a hinged mechanism 547 that connects actuator 546 to stems 543, and actuator 546 is configured to move vertically up and down along a direction indicated by line 586 such that stems 543 can be tilted relative to circumferential element 541.

In some embodiments, each one of the plurality of tissue-compression members 594 are made of a magnetic-resonance imaging (MRI)-safe material (e.g., nitinol or polymer or other compatible material). In some embodiments, tissue-compression members 594 include embedded MRI coils or coil portions, or have such coil portions attached to them.

Figure 5E:
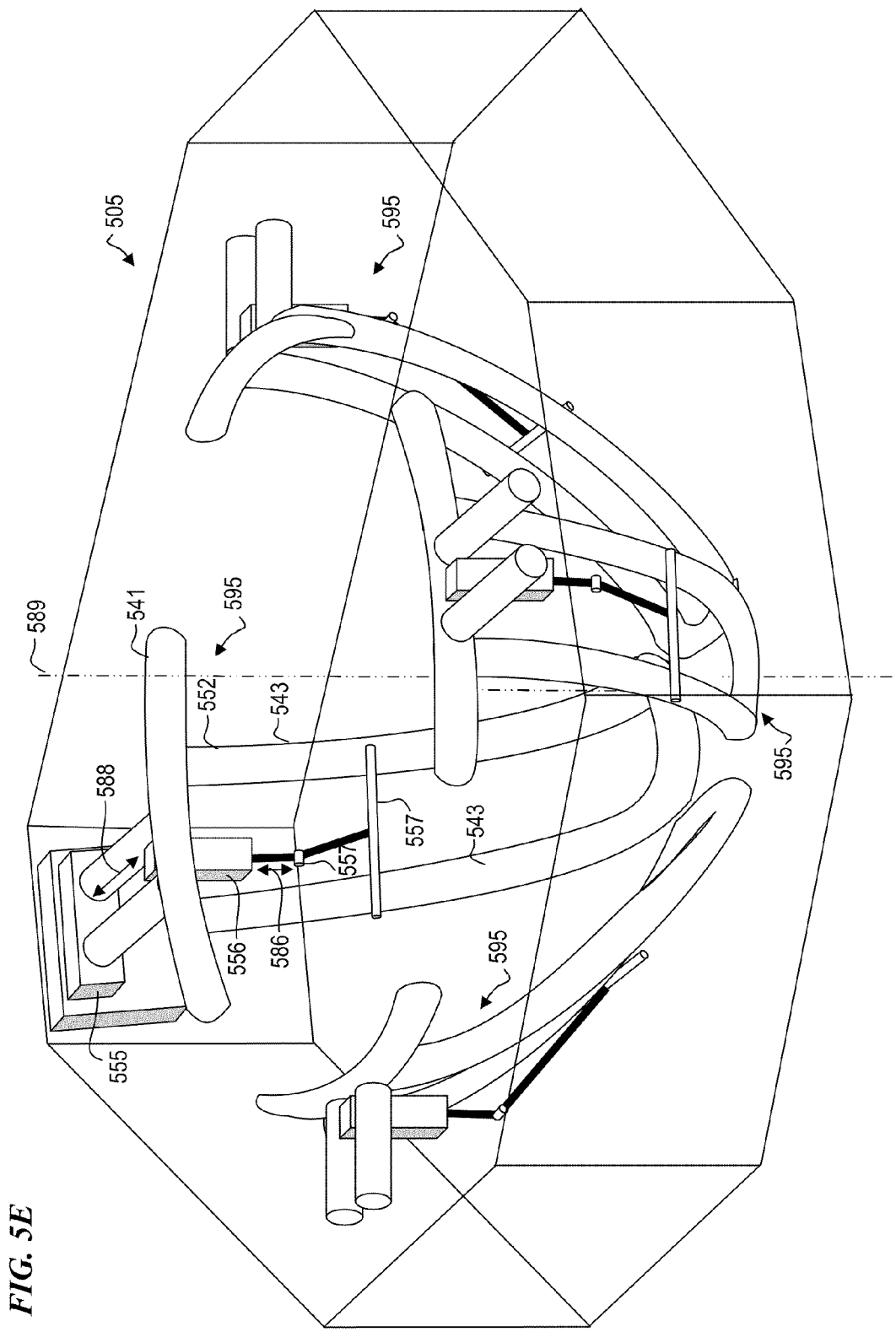
FIG. 5E is a perspective schematic view of a breast-compression cradle 505 having a plurality of tissue-compression members 595.

FIG. 5E is a perspective schematic view of a breast-compression cradle 505 having a plurality of tissue-compression members 595 (in the embodiment shown, four tissue-compression members 595 are used, while in other embodiments, other numbers of tissue-compression members 595 are used). In some embodiments, each one of the plurality of tissue-compression members 595 includes a circumferential element 551 that curves around at least a portion of a circumference 509 formed by the plurality of tissue-compression members 595. In some embodiments, one or more of the tissue-compression members 595 can also be moved up and down in order to better conform to the patient's rib cage (e.g., in some such embodiments, one can be moved upward under the arm of the patient to better compress and obtain MRI images of breast and lymph tissue there). In some embodiments, one or more of the circumferential elements 551 is springy and/or pliable, in order to provide comfort and/or a snugger fit. In some embodiments, each one of the plurality of tissue-compression members 595 includes a stem-shaped compression element 553, wherein stem 553 includes two upper ends 552 and a free lower end 554 such that stem 553 forms a U-Shape (in some embodiments, for example, upper ends 552 of the U-shaped stem 553 connect to circumferential element 551).

In some embodiments, stem 553 has a curved configuration such that when cradle 505 is in a compressed state (as illustrated in FIG. 5E), the lower end 554 of stem 553 is closer to center line 589 than the upper ends 552 of stem 553. In some embodiments, at least one of the plurality of tissue-compression members 595 includes two actuators (in some embodiments, for example, piezoelectric actuators). In some embodiments, for example, at least one of the plurality of tissue-compression members 595 includes a first actuator 555 and a second actuator 556. In some embodiments, first actuator 555 is configured to move radially inward and outward along a direction indicated by line 588 such that circumferential element 551 moves radially inward and outward. In some embodiments, second actuator 556 includes a hinged mechanism 557 that connects actuator 556 to stem 553, and actuator 556 is configured to move vertically up and down along a direction indicated by line 586 such that stem 553 can be tilted relative to circumferential element 551.

In some embodiments, each one of the plurality of tissue-compression members 595 are made of a magnetic-resonance imaging (MRI)-safe material (e.g., nitinol or polymer or other compatible material). In some embodiments, tissue-compression members 595 include embedded MRI coils or coil portions, or have such coil portions attached to them.

Figure 6B:
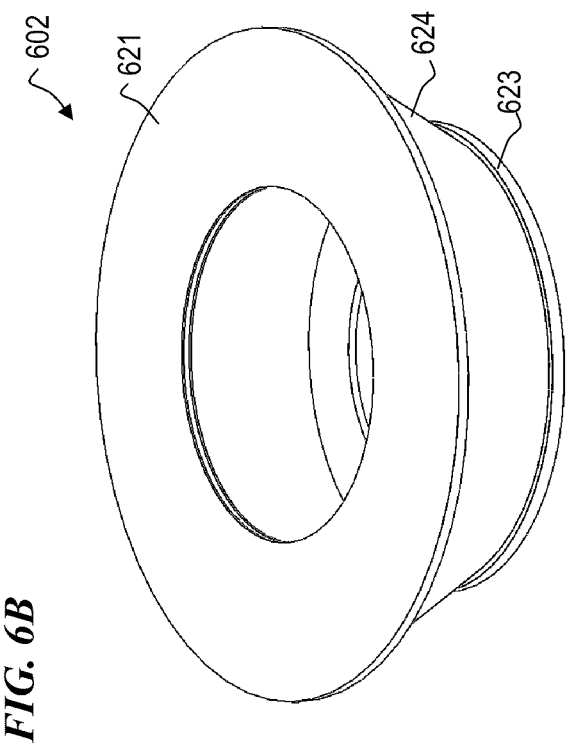
FIG. 6B is a perspective schematic view of an outer ring 602 having a larger-diameter upper ring 621 and a closed conical support brace 624.
Figure 6A:
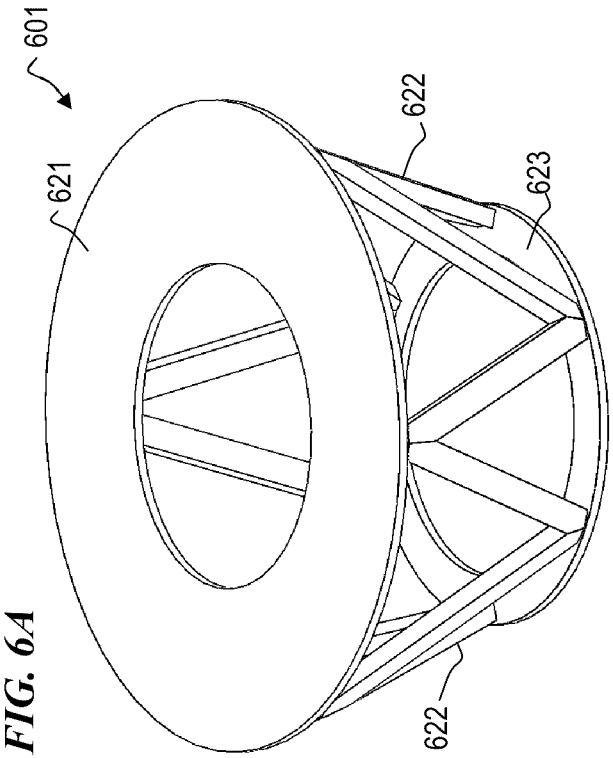
FIG. 6A is a perspective schematic view of an outer ring 601 having a larger-diameter upper ring 621 and alternating diagonal braces 622.

FIG. 6A is a perspective schematic view of an outer ring 601 having a larger-diameter upper ring 621, a lower ring 623, and alternating diagonal braces 622. The plurality of alternating diagonal braces 622 form triangular structures that provide additional stability in some embodiments.

FIG. 6B is a perspective schematic view of an outer ring 602 having a larger-diameter upper ring 621, a lower ring 623, and a closed conical support brace 624. The closed conical support brace 624 forms a wall structure that provides additional stability in some embodiments.

In some embodiments, one or more direct-mounted motors are each replaced with a Bowden-cable system.

Figure 7:
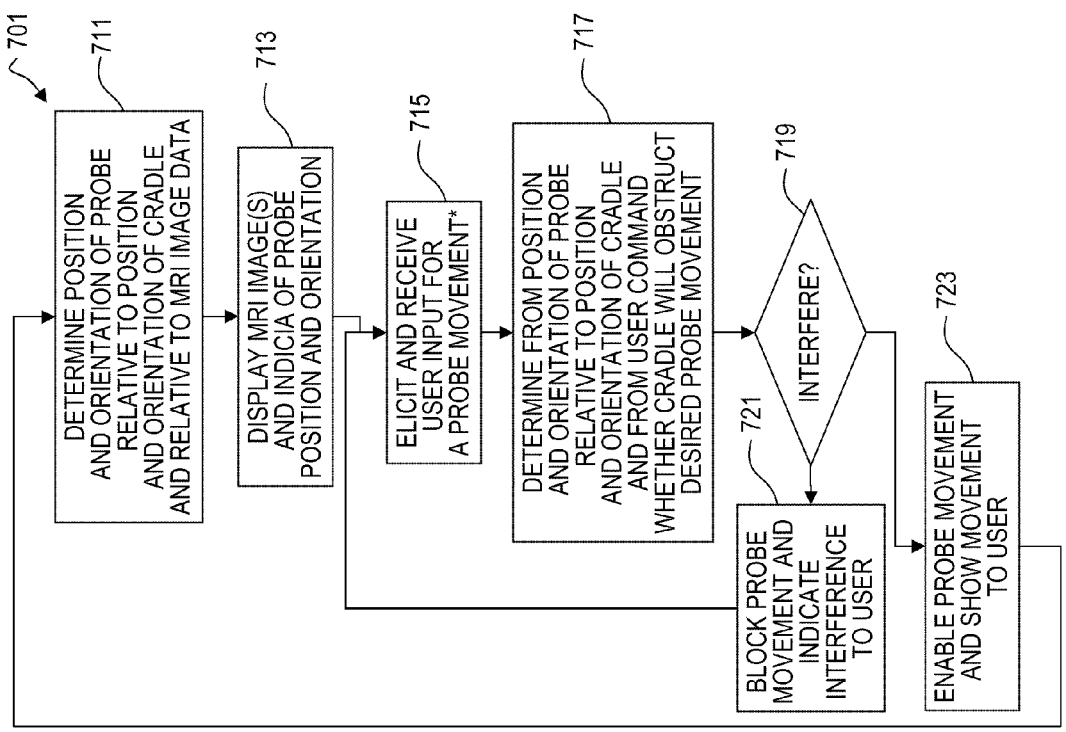
FIG. 7 is a flow-chart diagram of method 701 for performing an MRI-guided breast intervention, according to some embodiments of the present invention.

FIG. 7 is a flow-chart diagram of method 701 for performing an MRI-guided breast intervention, according to some embodiments of the present invention. In some embodiments, method 701 includes the following steps.

711. Determine the position and orientation of the intervention probe relative to the position and orientation of the compression cradle and also relative to the MRI image data.

713. Display the MRI image(s) and indicia of the intervention probe position and orientation on the user display.

715. Elicit and receive user input for a probe movement.

717. Determine from the position and orientation of the intervention probe relative to position and orientation of the compression cradle and from the input user command whether the compression cradle will obstruct desired probe movement.

719. If the compression cradle will interfere with the desired probe movement go to Step 721. If the compression cradle will not interfere with the desired probe movement, go directly to Step 723.

721. Block the desired probe movement, indicate interference to user on the user display and go back to Step 715.

723. Enable the desired probe movement, show the movement to user on the user display, and then proceed back to Step 711 of the present method 701.

Figure 8:
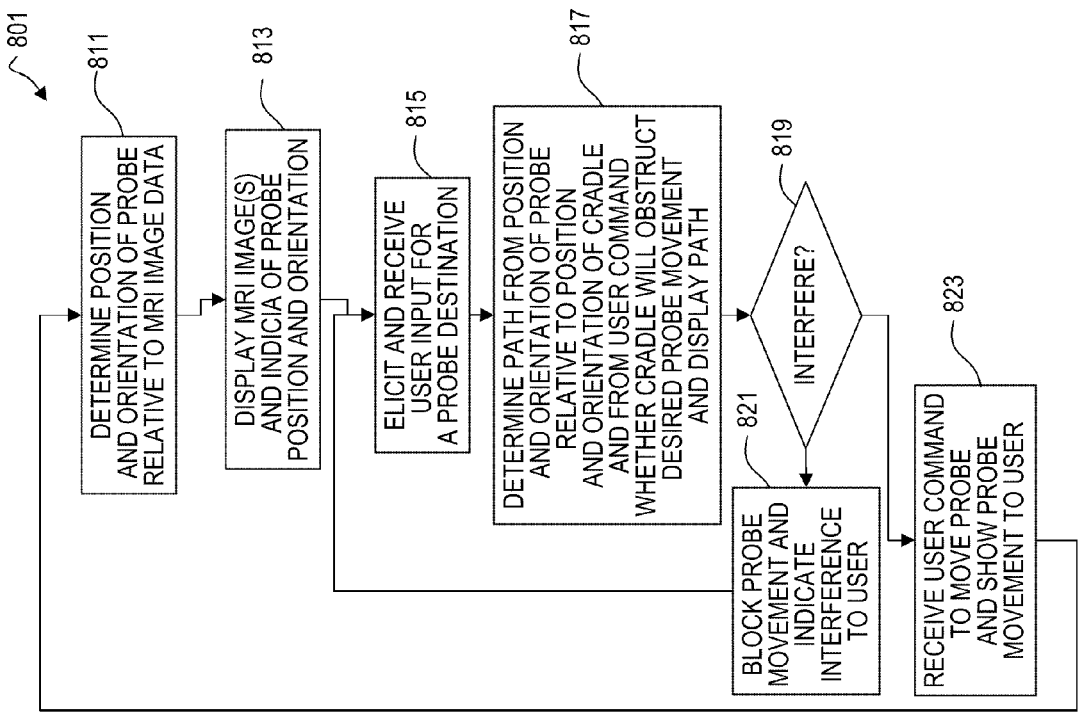
FIG. 8 is a flow-chart diagram of method 801 for performing an MRI-guided breast intervention, according to some embodiments of the present invention.

FIG. 8 is a flow-chart diagram of method 801 for performing an MRI-guided breast intervention, according to some embodiments of the present invention. In some embodiments, method 801 includes the following steps.

811. Determine the position and orientation of the probe relative to MRI image data.

813. Display the MRI image(s) and indicia of the probe position and orientation on the user display.

815. Elicit and receive user input for a desired probe movement.

817. Determine the probe movement path from the position and orientation of the probe relative to the position and orientation of the compression cradle and also from the user supplied command to determine whether cradle will obstruct the desired probe movement and then display the determined path.

819. If the compression cradle will interfere with the desired probe movement proceed to Step 821. If the compression cradle will not interfere with the desired probe movement, proceed directly to Step 823.

821. Block the desired probe movement, indicate interference to user on the user display that the probe movement has been blocked, and go back to Step 815.

823. Receive a user command to move the probe, show the probe movement to user, and proceed directly back to Step 811 of method 801.

Figure 9:
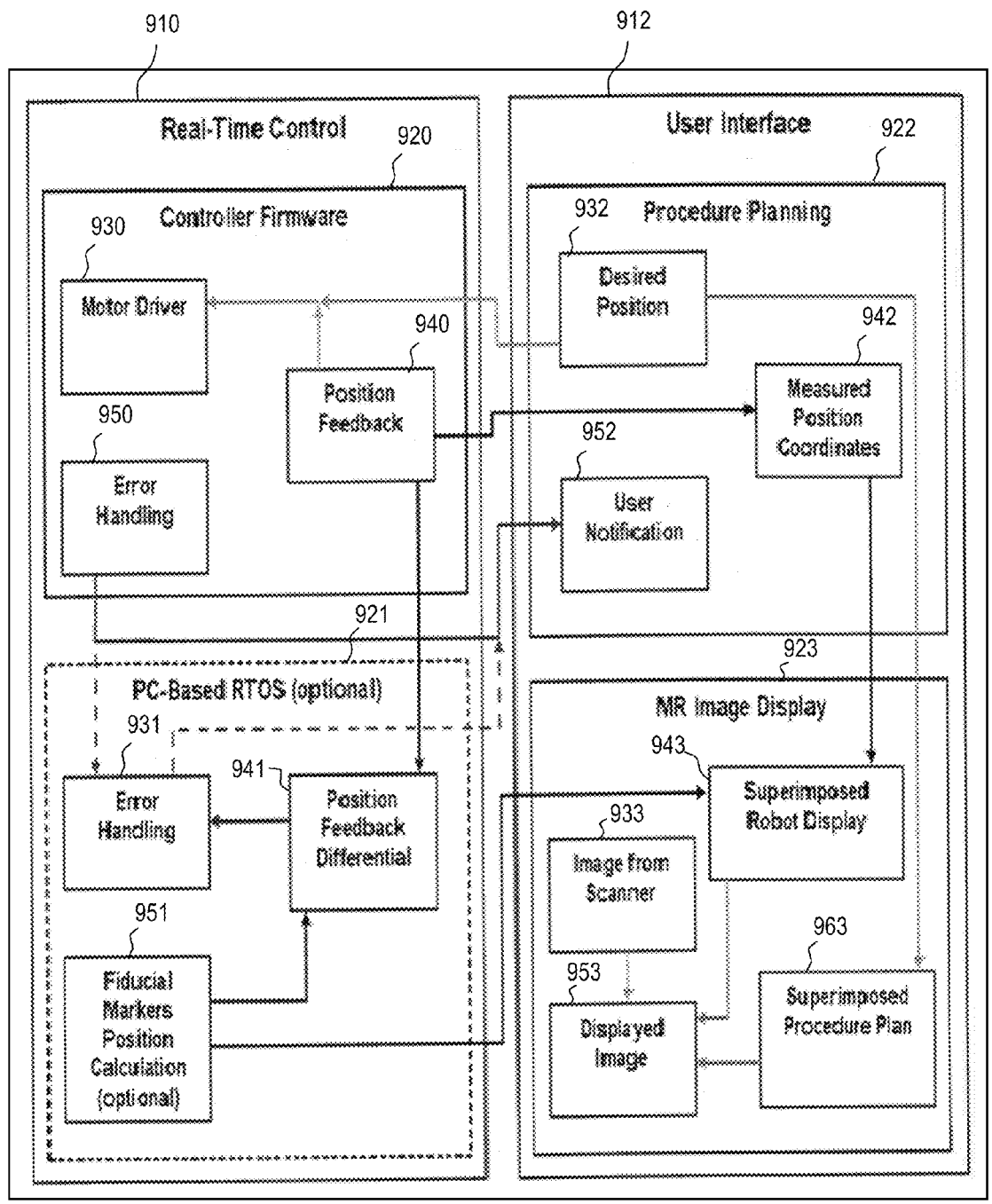
FIG. 9 is a block diagram of a multi-level control scheme 901.

FIG. 9 is a block diagram of a multi-level control scheme 901, according to some embodiments of the present invention. In some embodiments, multi-level control scheme 901 includes a real-time control system 920 having a controller firmware system 930 for controlling the actuators and servo motors of an MRI-guided breast-intervention apparatus of the present invention and, optionally, a personal-computer-based (PC-based) real-time operating system (RTOS) 921. In some embodiments, controller firmware system 930 includes a motor driver system 930, a position feedback system 940, and an error-handling system 950. In some embodiments, PC-based RTOS 921 includes an error-handling system 931, a position-feedback-differential system 941, and a fiducial-markers-position-calculation system 951.

In some embodiments, multi-level control scheme 901 further includes a user interface system 912 having a procedure planning system 922 and a magnetic resonance (MR) image display system 923. In some embodiments, procedure planning system 922 includes a desired-position input system 932, a measured-position coordinate outputting system 942, and a user-notification outputting system 952. In some embodiments, MR-image-display system 923 includes an image from scanner inputting system 933, a robot-display inputting system 943, a procedure-plan inputting system 963, and an image-display system 953 configured to display a superimposed composite image of the MRI image, the robot-display image, and the procedure-plan image user interface.

Another alternate embodiment still uses a primary rotary DOF, but instead of a linear-translational DOF unit, a secondary rotary DOF moves the outside height DOF to achieve a similar result. This still allows another angle for insertion.

In some embodiments, the present invention provides a magnetic resonance imaging (MRI) guided system with 3D-positioning capabilities. In some embodiments, the system includes five degree-of-freedom (DOF) units to position a probe: rotation, translation, height, declination, and insertion depth. In some embodiments, MRI-compatible piezoelectric motors designed for high magnetic fields are used in concert with new position encoders for precise remote control of probe position for MRI-guided interventions.

In some embodiments, the MR-guided interventional systems described herein use an actuator system having five degrees of freedom (DOF) to position a biopsy needle or therapy probe in the breast. Using MRI-compatible linear piezoelectric motors that may be located close to the image region of interest (ROI); the accuracy and repeatability of the positioning system can be significantly improved. The proposed operation of the system is as follows.

Due to the extremely high magnetic fields used in magnetic resonance imaging, great care must be taken in material selection and therefore component design (e.g., see F. G. Shellock and E. Kanal, "Magnetic resonance: bioeffects, safety, and patient management", Lippincott-Raven, 1996.; and K. Chinzei, R. Kikinis, and F. A. Jolesz, "MR Compatibility of Mechatronic Devices: Design Criteria," vol. 1679 of Medical Image Computing and Computer-Assisted Intervention—MICCAI '99, pp. 1020-1030. Heidelberg: Springer-Verlag, 1999). Specifically, nonmagnetic materials must be used to avoid forces on the device itself that can compromise its performance and may result in hazardous conditions for the patient or the medical personnel. In addition, materials near the region of interest should be non-conducting of electricity to avoid the generation of eddy currents. Eddy currents can distort the MR images and arise when the fast switching magnetic field gradients induce electric currents on the conductive parts of a device that are inside the scanner. Eddy currents may also cause undesired resistive heating of conductive objects.

In some embodiments, the breast is first stabilized using either a breast cradle or bilateral compression plates. A novel breast stabilization device or breast cradle is shown in FIG. 1, FIG. 2, and FIG. 3. The breast cradle of some embodiments provides substantially equal compression around the breast, as opposed to the compression achieved using typical bilateral compression plates that are conventionally used in both manual and robotic biopsy systems (e.g., see U. Fischera, L. Kopka, and E. Grabbe, "Magnetic resonance guided localization and biopsy of suspicious breast lesions," *Topics in Magnetic Resonance Imaging*, vol. 9, pp. 44-59, 1998; S. G. Orel, M. D. Schnall, R. W. Newman, C. M. Powell, M. H. Torosian, and E. F. Rosato, "MR imaging-guided localization and biopsy of breast lesions: Initial experience," *Radiology*, vol. 193, pp. 97-102, 1994; and C. K. Kuhl, A. Elevelt, C. C. Leutner, J. Gieseke, E. Pakos, and H. H. Schild, "Interventional breast MR imaging: clinical use of a stereotactic localization and biopsy device," *Radiology*, vol. 204, pp. 667-675, September 1997; W. Doler, U. Fischer, I. Metzget, D. Harder, and E. Grabbe, "Stereotaxic add-on device for MR-guided biopsy of breast lesions," *Radiology*, vol. 200, pp. 863-864, 1996.). This breast cradle, used in some embodiments of the present invention, operates as a scissor-pair ring linkage—all the links move together to at once compress the breast radially while pulling the breast away from the chest wall. In some embodiments, this mechanical linkage is designed to provide sufficient immobilization pressure to the breast while also allowing unprecedented access to the breast from many angles and orientations. Once the breast is stabilized, the procedure can be precisely planned and executed with full positional flexibility. In contrast, bilateral compression plates restrict access to the breast, and change to the angle of compression would, by moving the breast, would necessitate re-imaging the patient, relocating the target lesion, and re-planning the procedure (e.g., see B. T. Larson, N. V. Tsekos, A. G. Erdman, E. Yacoub, P. V. Tsekos, and I. G. Koutlas, "Design of an MRI-compatible stereotactic device for minimally invasive interventions in the breast," *Journal of Biomechanical Engineering*, vol. 126, pp. 458-465, August 2004; and S. O. R. Pfleiderer, J. R. Reichenback, T. Azhari, C. Marx, A. Malich, A. Schneider, J. Vagner, H. Fischer, and W. A. Kaiser, "Manipulator system for 14-gauge large core breast biopsies inside a highfield whole-body MR scanner," *Journal of Magnetic Resonance Imaging*, vol. 17, pp. 493-498, April 2003). The stabilization apparatus will be secured along with the breast coil to the patient couch inside the rotating apparatus (see FIG. 1). The patient's breast will be stabilized before the procedure outside of the scanner, immobilizing the breast yet allowing for sufficient blood flow.

The breast cradle linkage is shown in greater detail in FIG. 2 and FIG. 3. Each scissor pair consists of two links joined by a revolute joint near their centers. Spherical joints at the base and summit ends join one scissor pair to the next. By providing an actuation input such as a radial displacement at the base, the entire linkage collapses toward a common axis.

Secondly, the probe is rotated around the breast by three motors 124 spaced and equally distributed around the circumference of the positioning system (see FIG. 1B).

Previous designs have used less-MRI-compatible motors, required distant mounting and lengthy transmissions which contributed to significant inaccuracy problems (see B. T. Larson et al., "Design of an MRI-compatible stereotactic device for minimally invasive interventions in the breast," *Journal of Biomechanical Engineering*, vol. 126, pp. 458-465, August 2004). Certain piezoelectric motors, however, create very little artifact at 4T (a magnetic field of four Tesla). The proposed arrangement allows simple motor mounting and force distribution, ensuring that there are no unbalanced radial forces that could introduce excess bearing friction into the system compared to a single-motor or gear/belt driven system. Multiple motors may be driven by the same Nanomotion-brand amplifier, thereby eliminating any control scheme complexity by driving all motors equally. Due to the intermittent-contact nature of the piezoelectric motors, any misalignment during motion will be self-corrected to maintain a force balance.

Next, the height and declination of the probe is determined by two degrees of freedom: the probe inner height and outer height (see FIG. 1E). This arrangement is similar to that of previously developed models (see B. T. Larson et al., "Design of an MRI-compatible stereotactic device for minimally invasive interventions in the breast," *Journal of Biomechanical Engineering*, vol. 126, pp. 458-465, August 2004) except that linear motors are mounted directly onto the translation stage, rather than delivered by transmissions from rotational motors at the patient's feet. As with the rotation DOF, in some embodiments, this eliminates the significant gear backlash measured with the previous system and improves accuracy to sub-millimeter levels, an order-of-magnitude improvement.

Then, a new translational degree of freedom is proposed to provide a fifth positional degree of freedom. This new innovation will provide unparalleled flexibility in accessing the breast while avoiding obstacles. In some embodiments, one or the other of two options is used for this DOF: a directly-mounted motor system similar to other DOF's or a cable-driven system that has been previously demonstrated. In some embodiments, the directly-mounted system is likely better for precision and accuracy, but may be difficult or impractical to mount in the constrained space available. In other embodiments, the other option uses Bowden cables to transmit the motion of a remotely-mounted motor to the translation stage. Bowden cables include a wire inside a sheath, where these are arranged so that movement of the wire on one end will be translated to movement the other end, while the sheath may be flexed in any of a plurality of orientations without affecting the wire position. A common example of Bowden cables is the cable arrangement used for hand brakes on bicycles.

Finally, continuing with the inclusion of directly-mounted motors, in some embodiments, two opposing linear motors provide up to 32 N (thirty-two Newtons) of insertion force for the probe (see FIG. 4). Compared to using a flexible drive shaft connected to a screw drive for insertion as previously developed (see B. T. Larson et al., "Design of an MRI-compatible stereotactic device for minimally invasive interventions in the breast," *Journal of Biomechanical Engineering*, vol. 126, pp. 458-465, August 2004), this approach greatly increases the precision, speed, and insertion force to accommodate a number of different breast-cancer interventions. The approach also allows full 360-degree rotational access to the breast as opposed to the "tethered" flexible-shaft method.

Most MRI-guided procedures will involve multiple steps, such as anesthesia application, pre-insertion scalpel incision, and exchanging expandable trocars in addition to the probe insertion itself. To perform these tasks within a single MRI session, some embodiments of the insertion system are designed to accommodate a probe-exchanger system (see B. T. Larson, A. G. Erdman, and N. V. Tsekos, "An MRI-compatible probe exchanger for early diagnosis and treatment of breast cancer," in *Proceedings of the ASME* 2004 *Design Engineering Technical Conferences and Computers and Information in Engineering Conference*, ASME, 2004, which is incorporated herein by reference).

In some embodiments, basic design of parts and dimensioned drawings are performed with a solid modeling package such as SolidWorks (Natick, Mass.). In some embodiments, a companion package such as COSMOSMotion is used to analyze motor power, frictional losses, and component inertia. Finally, critical components are optimized for safety and performance using a finite-element-analysis (FEA) computer program such as COSMOSWorks Designer, also available with SolidWorks.

In some embodiments, precise, fully MRI-compatible position encoders are used to accurately decipher the position of the probe tip during operation. In some embodiments, each degree of freedom has an integrated encoder that measures its position to an accuracy of 0.1 mm or better. Using the forward kinematics of the system (e.g., adding up all the geometry aspects), the measured position of each DOF unit is used to calculate the probe-tip position. The proposed encoders use light (electromagnetic radiation of a suitable wavelength), transmitted through fiber optic cables, as a mechanism for "counting" hash marks (e.g., black striped on a clear substrate) to determine the position of a degree of freedom (see FIG. 8). By moving the light generators and sensors to outside the scanner room, electrical interference with the high-speed digital encoder signals can be avoided. In some embodiments, the encoder operates by simply counting lines. Two laser diodes generate two steady sources of light, which are transferred into the MRI-scanner room (where the high-magnetic-field apparatus is located) from a nearby control room via fiber optic cables. For simplicity, consider one light source as "A", the other as "B". These source cables bring light to a moving block attached to a DOF unit. Two receiver fiber optic cables catch the light, as they are mounted opposite the source cables. Between the source and receiver cables is the encoder strip, which is mounted on a fixed portion of the robot. The encoder strip is a thin, transparent sheet with small, equally-spaced hash marks that block light from either, neither, or both sources. In some embodiments, the received light is brought back outside of the scanner room to light detectors. These light detectors each produce a digital signal depending on whether light is sensed or not. Movement is determined by "counting" the hash marks as the dark lines on the encoder strip break a light stream between each of a plurality of source/receiver optical-fiber pairs. In some embodiments, the "A" and "B" of source/receiver cables are fixed 90-degrees out-of-phase or in "quadrature" relative to clear and opaque stripes (e.g., in some embodiments, the clear and opaque stripes are each twice as wide as the distance between ends of the fibers such that during transit of one pair of the opaque-clear stripes, 25% of the distance will have both light beams blocked by an opaque stripe, 25% of the distance will have "A" blocked but "B" not blocked, 25% of the distance will have both beams not blocked, and 25% of the distance will have "A" not blocked but "B" blocked. This quadrature arrangement allows distinct determination of whether the system should count "up" or "down", based on the relation between signals (see both FIG. 9 and FIG. 10). This is a common encoder arrangement and is compatible with most servo-motor controllers. To achieve finer precision, thinner optical fibers are used and spaced closer together, and narrower stripes are used. In other embodiments, additional optical fibers and additional stripes of different widths are used to determine absolute position (e.g., by using 16 stripe widths (each being a different integer power of two times the smallest stripe width) and 17 fibers, an absolute position can be determined to a precision of one in $2^{17}$ (131,072); for example if the minimum stripe width is 2 microns (such that the pair of one opaque stripe and one transparent stripe is 4 microns wide and two fibers are used to determine quadrature and are spaced 1 micron center-to-center), and the widest stripe is 131072 microns, then the position can be determined with a resolution up to about 1 micron across a distance of more than 262 mm).

In some embodiments, a multi-layer control scheme controls the mission-critical components in real-time to ensure patient safety. The capabilities of the IGI system and breast-imaging RF coil are integrated with a control system and user interface to create a fully functional system.

A new multi-layer software system is used to control the probe positioning system (see FIG. 9). In some embodiments, the "real-time control" layer is performed by a real-time operating system (RTOS) in concert with an integrated servo-motor controller. The digital quadrature encoders used are able to attach to this and most other servo controllers. This closed servo-control loop reads position measurements with sub-millimeter precision in real-time, compares them with the desired position (which is determined from data input by the user), and makes immediate adjustments to the motor driver signals to correct any position errors. In addition, mission-critical decisions and error handling are incorporated into the controller firmware. The SPiiPlus PCI controller used in some embodiments has integrated high-speed error inputs and limit-switch inputs, as well as firmware routines suitable for handling such events. In addition, the controller has digital inputs and outputs for basic start/stop buttons, manual override, control panel lights, simple biopsy gun triggers, etc. Using the controller for these functions ensures the fastest reaction time and minimizes any errors that might be possible designing a PC-based system. If additional real-time processing must be performed outside of the controller firmware, a PC-based RTOS is used to ensure patient safety and system functionality.

In contrast, in some embodiments, the "user interface" layer is a lower-priority process, running either on a separate computer or in another thread on the RTOS. Imaging information from MRI is integrated into the user interface for registration of the images with the position of the biopsy needle or therapy probe, as determined by the encoders. Registration techniques are empirically validated as to the accuracy of probe tip position in bench studies and tissue-phantom studies acquired at comparable spatial resolution to in vivo data. The accuracy and precision of probe tip localization on anatomical and parametric maps, based on the encoder data, are compared by targeting phantom lesions, either independent of, and/or including multiple 3D data sets. In some embodiments, provisions are made for active fiducial markers, micro-coils that can be used to pinpoint position with NMR-imaging techniques to provide redundant positional data to ensure patient safety and proper operation.

In some embodiments, communication between the real-time and user-interface modules is achieved with standard RS-232 (serial) electronics, USB (universal serial bus) electronics or the like for mission-critical signals. Constant updating of position variables, end stops, error signals, and user input occur over these dedicated, high-speed lines of communication. Other, non-critical communications are performed using off-the-shelf hardware that follow Ethernet standards for ease-of-use and ultimate flexibility.

Figure 10:
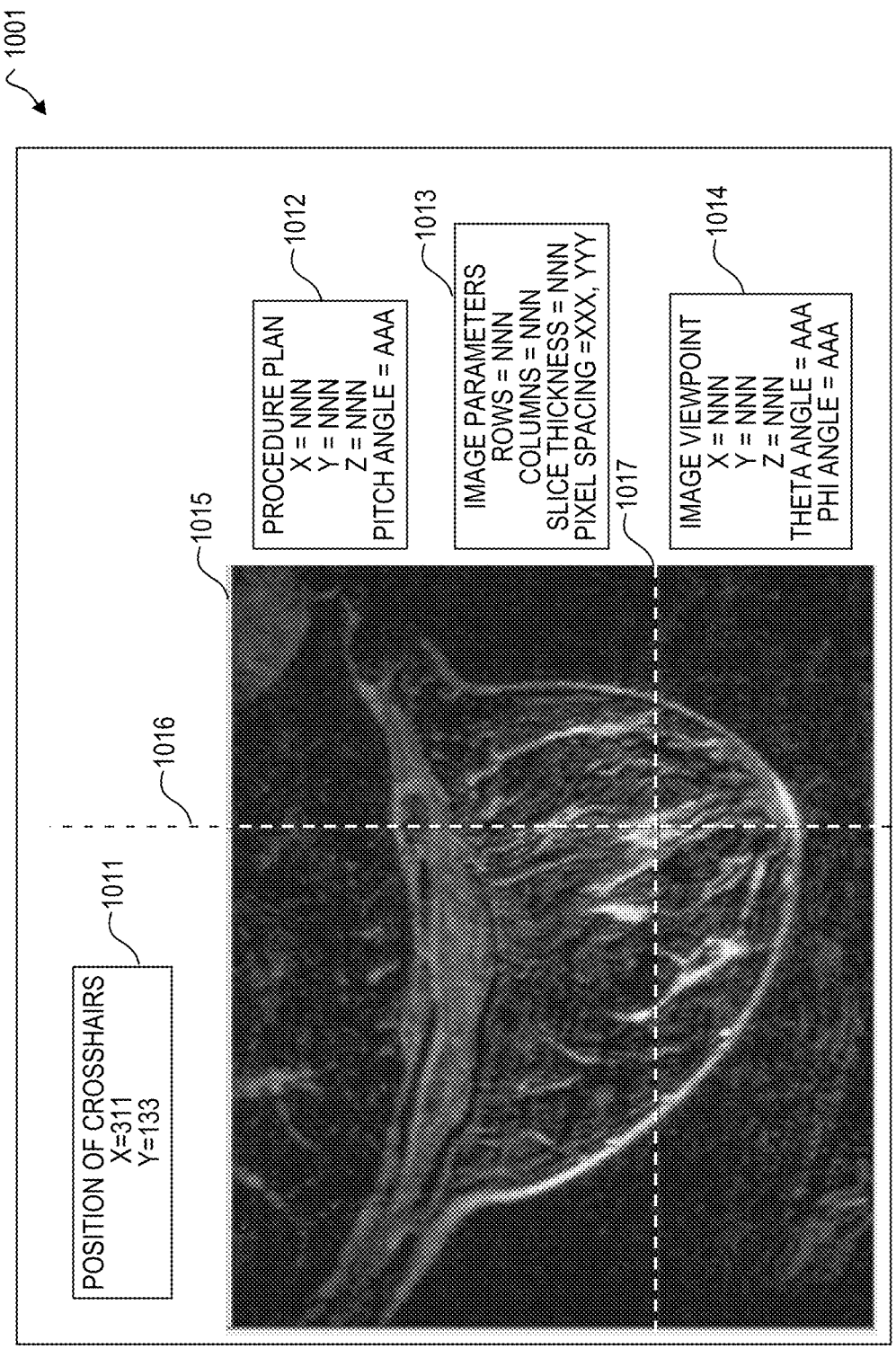
FIG. 10 is a generated image of a graphical user interface (GUI) 1001.

A portion of the user interface utilized for some embodiments is shown in FIG. 10. Using MR images taken during the procedure, the operator can either enter desired target coordinates or use a mouse to direct the crosshairs. The 3D coordinates of selected point are determined using image parameters from the scanner and a registration process.

FIG. 10 is a schematic depiction of a screen shot 1001 of a graphical user interface (GUI), according to some embodiments of the present invention. In some embodiments, screen shot 1001 includes a plurality of images and information superimposed on a single graphical user interface to generate a composite picture of an MRI-guided breast intervention as provided by the present invention. In some embodiments, screen shot 1001 includes an MRI image 1015 of a breast of a patient undergoing a medical procedure (e.g., a breast-tissue biopsy), an image of vertical crosshair 1016 and horizontal crosshair 1017 superimposed over the MRI image 1015 to graphically locate the position of the intervention probe (i.e., the intersection of the vertical crosshair 1016 with the horizontal crosshair 1017) with respect to the breast of the patient and more specifically with respect to the breast tissue to be biopsied. In addition to the image data, screen shot 1001 further includes a plurality of information related to the medical procedure, including crosshair values 1011, procedure plan information 1012 related to the user supplied probe position coordinates and angle, MRI image information 1013 and image viewpoint information 1014.

In some embodiments, the present invention provides a method for fabricating a pantomesh. The method includes providing a plurality of pairs of links, wherein each link has a first end and a second end, wherein each pair of links includes a first link and a second link, and wherein the plurality of pairs of links includes a first pair and a second pair, providing a plurality of revolute joints, including a first revolute joint and a second revolute joint, providing a plurality of spherical joints includes a first spherical joint and a second spherical joint. The method further includes connecting a location between the first end and the second end of the first link of the first pair to a location between the first end and the second end of the second link of the first pair using the first revolute joint, connecting a location between the first end and the second end of the first link of the second pair to a location between the first end and the second end of the second link of the second pair using the second revolute joint, connecting the first end of the first link of the first pair of links to the first end of the second link of the second pair of links using the first spherical joint, and connecting the second end of the second link of the first pair of links to the second end of the first link of the second pair of links using the second spherical joint (? equation).

In some embodiments of the method, the providing of the plurality of pairs of links further includes providing a third pair and a fourth pair, the providing the plurality of revolute joints further includes providing a third revolute joint and a fourth revolute joint, and the providing of the plurality of spherical joints further includes providing a third spherical joint. The method further includes: connecting a location between the first end and the second end of the first link of the third pair to a location between the first end and the second end of the second link of the third pair suing the third revolute joint, connecting a location between the first end and the second end of the first link of the fourth pair to a location between the first end and the second end of the second link of the fourth pair using the fourth revolute joint, connecting the first end of the first link of the third pair of links to the first end of the second link of the fourth pair of links, using the second spherical joint, and connecting the second end of the second link of the third pair of links to the second end of the first link of the fourth pair of links using the third spherical joint.

In some embodiments, the present invention provides a first apparatus that includes a pantomesh 200 which has a plurality of pairs of links, wherein each link has a first end and a second end, wherein each pair of links includes a first link and a second link, and wherein the plurality of pairs of links includes a first pair 210 and a second pair 210; a plurality of revolute joints, including a first revolute joint 213 and a second revolute joint 213, wherein the first revolute joint 213 connects a location between the first end and the second end of the first link 211 of the first pair 210 to a location between the first end and the second end of the second link 212 of the first pair 210, and the second revolute joint 213 connects a location between the first end and the second end of the first link 211 of the second pair 210 to a location between the first end and the second end of the second link 212 of the second pair 210; and a plurality of spherical joints that includes a first spherical joint 216 and a second spherical joint 219, wherein the first spherical joint 216 connects the first end of the first link 211 of the first pair of links 210 to the first end of the second link 212 of the second pair of links 210, and the second spherical joint 219 connects the second end of the second link 212 of the first pair of links 210 to the second end of the first link 211 of the second pair of links 210.

In some embodiments of the first apparatus, the plurality of pairs of links further includes a third pair 210 and a fourth pair 210, the plurality of revolute joints further includes a third revolute joint 213 and a fourth revolute joint 213, wherein the third revolute joint 213 connects a location between the first end and the second end of the first link 211 of the third pair 210 to a location between the first end and the second end of the second link 212 of the third pair 210, and the fourth revolute joint 213 connects a location between the first end and the second end of the first link 211 of the fourth pair 210 to a location between the first end and the second end of the second link 212 of the fourth pair 210, and the plurality of spherical joints further includes a third spherical joint 218, a fourth spherical joint 216 and a fifth spherical joint 216. The first spherical 216 joint also connects the first end of the second link 212 of the third pair of links to the first end of the first link 211 of the fourth pair of links, the third spherical joint 218 connects the first end of the first link 211 of the third pair of links to the second end of the second link 212 of the first pair of links 210, the fourth spherical joint 216 connects the first end of the second link 212 of the fourth pair 210 to the second end of the first link 211 of the second pair 210, and the fifth spherical joint 216 connects the second end of the first link 211 of the third pair 210 to the second end of the second link 212 of the fourth pair 210.

In some embodiments, the present invention provides a second apparatus that includes a pantomesh that includes: a first plurality of pantomesh elements including a first pantomesh element, a second pantomesh element and an Nth pantomesh element, where N is an integer larger than 2, and wherein each one of the first plurality of pantomesh elements includes: a pair of links including a first link and a second link, wherein each link of the pair of links has a first end and a second end; a revolute joint wherein the revolute joint connects a location between the first end and the second end of the first link to a location between the first end and the second end of the second link; and a plurality of spherical joints that includes a first spherical joint, a second spherical joint, a third spherical joint, and a fourth spherical joint, wherein the first spherical joint is attached to the first end of the first link, the second spherical joint is attached to the second end of the first link, the third spherical joint is attached to the first end of the second link, and the fourth spherical joint is attached to the second end of the second link, wherein the first and third spherical joints of the first pantomesh element connect to the second and fourth spherical joints, respectively, of the second pantomesh element of a first row of the first plurality of pantomesh elements, and the second and fourth spherical joints of the first pantomesh element connect to the first and third spherical joints, respectively, of the $N^{th}$ pantomesh element of the first row, and wherein a first line that extends through the first spherical joint and the third spherical joint of the first pantomesh element forms a first variable angle with a second line that extends through the second spherical joint and the fourth spherical joint of the first pantomesh element, and wherein the first variable angle changes as a distance between the first and third spherical joints increases.

In some embodiments, the present invention provides a computer-controlled method for performing a medical procedure in a magnetic-resonance-imaging (MRI) machine. This method includes compressing bodily tissue of a portion of a patient using a plurality of elongate members including a first elongate member, a second elongate member and a third elongate member, each of the plurality of elongate members having a width and a length wherein the width is narrower than the length, such that a first area of biological tissue is exposed between the first member and the second member and a second area of biological tissue is exposed between the first member and the third member; and under control of a computer system: activating a high-strength magnetic field of at least one Tesla that extends through the portion of the patient; obtaining MRI image data of the portion of the patient; and based on the obtained MRI image data, moving a medical-procedure probe to a position and an orientation that addresses a selected one of the first area of exposed biological tissue and the second area of exposed biological tissue, and then extending the probe into the selected exposed biological tissue of the portion of the patient.

In some embodiments of the method, the portion of the patient is a breast of the patient, and wherein the first area of exposed biological tissue is a first area of skin of the breast and the second area of exposed biological tissue is a second area of skin of the breast, and wherein the probe includes a biopsy needle, and wherein the method further includes, under the control of the computer system, obtaining a biopsy sample of tissue from a lesion in the breast.

Some embodiments of the method further include using the computer system, determining the position and the orientation of the probe; and displaying an MRI image of the portion of the patient from a viewpoint of the probe.

Some embodiments of the method further include using the computer system, determining the position and the orientation of the probe; using the computer system, determining positions and orientations of the plurality of elongate members; and based on the determined position and orientation of the probe and the determined positions and orientations of the plurality of elongate members, controlling movement of the probe in order to automatically avoid interference between the probe and the plurality of elongate members.

Some embodiments of the method further include using the computer system, determining positions and orientations of the plurality of elongate members; displaying an MRI image of the portion of the patient; receiving user input that specifies a desired target of the probe; using the computer system and based on the user input and the determined positions and orientations of the plurality of elongate members, moving the probe to a position and orientation relative to the plurality of elongate members that avoids interference between the probe and the plurality of elongate members as the probe is extended; and extending the probe into the selected exposed biological tissue between two of the plurality of elongate members.

Some embodiments of the method further include using the computer system, determining the position and the orientation of the probe and determining positions and orientations of the plurality of elongate members; and displaying an image of the portion of the patient along with indicia (one or more icons or other graphical indications) of the position and the orientation of the probe and the positions and the orientations of the plurality of elongate members.

In some embodiments of the method, the portion of the patient is a breast of the patient, and wherein the first area of exposed biological tissue is a first area of skin of the breast and the second area of exposed biological tissue is a second area of skin of the breast, and wherein the probe includes a biopsy needle, and wherein the method further includes, under the control of the computer, obtaining a biopsy sample of tissue from a lesion in the breast, and the method further includes using the computer system, determining the position and the orientation of the probe; displaying an MRI image of the portion of the patient from a viewpoint of the probe; using the computer system, determining positions and orientations of the plurality of elongate members; and based on the determined position and orientation of the probe and the determined positions and orientations of the plurality of elongate members, controlling movement of the probe in order to automatically avoid interference between the probe and the plurality of elongate members.

In some embodiments, the present invention provides an apparatus that includes a fixture that includes a plurality of elongate members including a first elongate member, a second elongate member and a third elongate member, each of the plurality of elongate members having a width and a length wherein the width is narrower than the length, wherein the plurality of elongate members are configured to be moved to compress bodily tissue of a portion of a patient such that a first area of biological tissue is exposed between the first member and the second member and a second area of biological tissue is exposed between the first member and the third member, and wherein the fixture is made of at least one material that is compatible with use in an magnetic-resonance-imaging (MRI) machine when the MRI machine is in operation; an electrically controlled actuator having a receiver for a medical-procedure probe; and a computer system operatively coupled to the actuator to control a movement of the probe, wherein the computer is configured to receive MRI image data of the portion of the patient and to receive input user commands, and wherein the computer is configured, based on the obtained MRI image data, to control the actuator to move the medical-procedure probe to a position and an orientation that addresses a selected one of the first area of exposed biological tissue and the second area of exposed biological tissue, and then based on the received user commands, to extend the probe into the selected exposed biological tissue of the portion of the patient.

In some embodiments of the apparatus, the portion of the patient is a breast of the patient, and wherein the first area of exposed biological tissue is a first area of exposed skin of the breast and the second area of exposed biological tissue is a second area of exposed skin of the breast, and wherein the probe includes a biopsy needle, and wherein the electrically controlled actuator is configured, under the control of the computer system, to obtain a biopsy sample of tissue from a lesion in the breast.

Some embodiments of the apparatus further include a display unit operatively coupled to the computer and configured to display an MRI image of the portion of the patient; an input device operatively coupled to the computer and configured to receive user input that specifies a desired target of the probe relative to the displayed MRI image, wherein the computer system is configured to determine the position and the orientation of the probe, to determine positions and orientations of the plurality of elongate members, and wherein the computer system is configured, based on the user input and the determined positions and orientations of the plurality of elongate members, to move the probe to a position and orientation relative to the plurality of elongate members that addresses a selected one of the first and second areas of exposed skin and that avoids interference between the probe and the plurality of elongate members as the probe is extended, and to extend the probe into the selected area of exposed skin between two of the plurality of elongate members.

In some embodiments of the apparatus, the computer system is configured to determine the position and the orientation of the probe, and based on the received MRI image data and the determined position and orientation of the probe to calculate an MRI image of the portion of the patient from a viewpoint of the probe; and wherein the apparatus further includes a display operatively coupled to the computer to display the calculated MRI image of the portion of the patient from a viewpoint of the probe.

In some embodiments of the apparatus, the computer system is configured to determine the position and the orientation of the probe, to determine positions and orientations of the plurality of elongate members; and based on the determined position and orientation of the probe and the determined positions and orientations of the plurality of elongate members, to control the actuator to move the probe in order to automatically avoid interference between the probe and the plurality of elongate members.

Some embodiments of the apparatus further include a display unit operatively coupled to the computer, wherein the computer system is configured to determine the position and the orientation of the probe, to determine positions and orientations of the plurality of elongate members, and to couple signals to the display unit to display an image of the portion of the patient along with indicia of the position and the orientation of the probe and the positions and the orientations of the plurality of elongate members.

Some embodiments of the apparatus further include a display unit operatively coupled to the computer, wherein the portion of the patient is a breast of the patient, and wherein the first area of exposed biological tissue is a first area of skin of the breast and the second area of exposed biological tissue is a second area of skin of the breast, and wherein the probe includes a biopsy needle, and wherein the computer is configured to control the actuator to obtain a biopsy sample of tissue from a lesion in the breast, and wherein the computer system is configured to determine positions and orientations of the plurality of elongate members, and to determine the position and the orientation of the probe, and to display an MRI image of the portion of the patient from a viewpoint of the probe; and based on the determined position and orientation of the probe and the determined positions and orientations of the plurality of elongate members, to control the actuator to move the probe in order to automatically avoid interference between the probe and the plurality of elongate members.

In some embodiments, the present invention provides an apparatus that includes a tissue-compression fixture having a plurality of members that are configured to be moved to compress bodily tissue of a portion of a patient from a plurality of at least three directions, wherein the fixture is configured such that each of a plurality of areas of biological tissue are exposed between the plurality of members, and wherein the fixture is compatible with use in an magnetic-resonance-imaging (MRI) machine when the MRI machine is in operation; an electrically controlled actuator having a receiver for a medical-procedure probe; and a computer system operatively coupled to the actuator to control a movement of the probe, wherein the computer is configured to receive input user commands, and based on the received user commands, to move the actuator to a selected one of a plurality of different positions around the tissue-compression fixture and to then extend the probe into biological tissue of the portion of the patient.

In some embodiments of the apparatus, the portion of the patient is a breast of the patient, and wherein the exposed plurality of areas of biological tissue include a first exposed area of skin of the breast and a second area of exposed area of skin of the breast, and wherein the probe includes a biopsy needle, and wherein the electrically controlled actuator is configured, under the control of the computer, to obtain a biopsy sample of tissue from a lesion in the breast.

Some embodiments of the apparatus further include a display unit operatively coupled to the computer and configured to display an MRI image of the portion of the patient; an input device operatively coupled to the computer and configured to receive user input that specifies a desired target of the probe relative to the displayed MRI image, wherein the computer system is configured to determine the position and the orientation of the probe, to determine positions and orientations of the plurality of fixture members, and wherein the computer system is configured, based on the user input and the determined positions and orientations of the plurality of fixture members, to move the probe to a position and orientation relative to the plurality of fixture members that addresses a selected one of the first and second exposed areas of skin and that avoids interference between the probe and the plurality of fixture members as the probe is extended, and to extend the probe into the selected exposed area of skin between two of the plurality of fixture members.

In some embodiments of the apparatus, the computer system is configured to determine the position and the orientation of the probe, and based on the received MRI image data and the determined position and orientation of the probe to calculate an MRI image of the portion of the patient from a viewpoint of the probe; and wherein the apparatus further includes a display operatively coupled to the computer to display the calculated MRI image of the portion of the patient from a viewpoint of the probe.

In some embodiments of the apparatus, the computer system is configured to determine the position and the orientation of the probe, to determine positions and orientations of the plurality of fixture members; and based on the determined position and orientation of the probe and the determined positions and orientations of the plurality of fixture members, to control the actuator to move the probe in order to automatically avoid interference between the probe and the plurality of fixture members.

Some embodiments of the apparatus further include a display unit operatively coupled to the computer, wherein the computer system is configured to determine the position and the orientation of the probe, to determine positions and orientations of the plurality of fixture members, and to couple signals to the display unit to display an image of the portion of the patient along with indicia of the position and the orientation of the probe and the positions and the orientations of the plurality of elongate members.

Some embodiments of the apparatus further include a display unit operatively coupled to the computer, wherein the portion of the patient is a breast of the patient, and wherein the exposed plurality of areas of biological tissue include a first exposed area of skin of the breast and a second area of exposed area of skin of the breast, and wherein the probe includes a biopsy needle, and wherein the computer is configured to control the actuator to obtain a biopsy sample of tissue from a lesion in the breast, and wherein the computer system is configured to determine positions and orientations of the plurality of elongate members, and to determine the position and the orientation of the probe, and to display an MRI image of the portion of the patient from a viewpoint of the probe; and based on the determined position and orientation of the probe and the determined positions and orientations of the plurality of elongate members, to control the actuator to move the probe in order to automatically avoid interference between the probe and the plurality of elongate members.

In some embodiments, the fixture includes a pantomesh that includes a plurality of revolute joints, including a first revolute joint and a second revolute joint; a plurality of spherical joints including a first spherical joint and a second spherical joint, wherein a location between the first end and the second end of the first link of the first pair is connected to a location between the first end and the second end of the second link of the first pair using the first revolute joint; a location between the first end and the second end of the first link of the second pair is connected to a location between the first end and the second end of the second link of the second pair using the second revolute joint; the first end of the first link of the first pair of links is connected to the first end of the second link of the second pair of links using the first spherical joint; and the second end of the second link of the first pair of links is connected to the second end of the first link of the second pair of links using the second spherical joint.

In some embodiments, the fixture includes a pantomesh that includes: a first plurality of pantomesh elements including a first pantomesh element, a second pantomesh element and an $N^{th}$ pantomesh element, where N is an integer larger than 2. Each one of the first plurality of pantomesh elements includes: a pair of links including a first link and a second link, wherein each link of the pair of links has a first end and a second end, a revolute joint wherein the revolute joint connects a location between the first end and the second end of the first link to a location between the first end and the second end of the second link, and a plurality of spherical joints that includes a first spherical joint, a second spherical joint, a third spherical joint, and a fourth spherical joint, wherein the first spherical joint is attached to the first end of the first link, the second spherical joint is attached to the second end of the first link, the third spherical joint is attached to the first end of the second link, and the fourth spherical joint is attached to the second end of the second link. In some embodiments, the first and third spherical joints of the first pantomesh element connect to the second and fourth spherical joints, respectively, of the second pantomesh element of a first row of the first plurality of pantomesh elements, and the second and fourth spherical joints of the first pantomesh element connect to the first and third spherical joints, respectively, of the $N^{th}$ pantomesh element of the first row, and wherein a first line that extends through the first spherical joint and the third spherical joint of the first pantomesh element forms a first variable angle with a second line that extends through the second spherical joint and the fourth spherical joint of the first pantomesh element, and wherein the first variable angle changes as a distance between the first and third spherical joints increases. In some embodiments, the second pantomesh element of the first row further connects to the $N^{th}$ pantomesh element of the first row with the spherical joints at the ends of the corresponding links of each pantomesh element thus forming a closed chain or row of pantomesh elements It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A computer-controlled method for performing a medical procedure in a magnetic-resonance-imaging (MRI) machine, the method comprising:

compressing bodily tissue of a portion of a patient using a plurality of pairs of elongate links including a first pair of links, a second pair of links and an $N^{th}$ pair of links, where N is an integer larger than 2, and wherein each one of the plurality of pairs of links includes:

a first link and a second link, wherein each link of the pair of links has a first end and a second end;

a revolute joint wherein the revolute joint connects a location between the first end and the second end of the first link to a location between the first end and the second end of the second link; and a plurality of spherical joints that includes a first spherical joint, a second spherical joint, a third spherical joint, and a fourth spherical joint, wherein the first spherical joint is attached to the first end of the first link, the second spherical joint is attached to the second end of the first link, the third spherical joint is attached to the first end of the second link, and the fourth spherical joint is attached to the second end of the second link, wherein the first and fourth spherical joints of the first pair of links are the third and second spherical joints, respectively, of the second pair of links of a row of the plurality of pairs of links, and the third and second spherical joints of the first pair of links are the first and fourth spherical joints, respectively, of the $N^{th}$ pair of links of the row;

such that a first area of biological tissue is exposed between the first pair of links and the second pair of links and a second area of biological tissue is exposed between the first pair of links and the $N^{th}$ pair of links; and under control of a computer system:

activating a high-strength magnetic field of at least one Tesla that extends through the portion of the patient;

obtaining MRI image data of the portion of the patient; and based on the obtained MRI image data, moving a medical-procedure probe to a position on a circumference of a first circle that is perpendicular to and surrounding a first rotational axis that passes through the biological tissue and an orientation that addresses a selected one of the first area of exposed biological tissue and the second area of exposed biological tissue using a plurality of positional degrees of freedom to position the probe relative to the compressed bodily tissue, wherein the plurality of positional degrees of freedom include a first degree of freedom that determines a first coordinate position of the probe on the circumference of the first circle and at a first rotational angle relative to the first rotational axis that passes through the biological tissue, a second degree of freedom that determines a height of the probe, a third degree of freedom that determines a pitch angle of the probe, a fourth degree of freedom that determines a second rotational angle of the probe relative to a second rotational axis that is not the first rotational axis, and a fifth degree of freedom defined by a probe-extension line that extends along a longitudinal axis of the probe, and then extending the probe along the probe-extension line into the selected exposed biological tissue of the portion of the patient using the fifth degree of freedom.

2. The method of claim 1, wherein the portion of the patient is a breast of the patient, and wherein the first area of exposed biological tissue is a first area of skin of the breast and the second area of exposed biological tissue is a second area of skin of the breast, and wherein the probe includes a biopsy needle, and wherein the method further includes, under the control of the computer system, obtaining a biopsy sample of tissue from a lesion in the breast.

3. The method of claim 1, further comprising:
using the computer system, determining the position and the orientation of the probe; and
displaying an MRI image of the portion of the patient from a viewpoint of the probe.

4. The method of claim 1, further comprising:
using the computer system, determining the position and the orientation of the probe;
using the computer system, determining positions and orientations of the links of the plurality of pairs of links; and
based on the determined position and orientation of the probe and the determined positions and orientations of the links, controlling movement of the probe in order to automatically avoid interference between the probe and the links.

5. The method of claim 1, further comprising:
using the computer system, determining positions and orientations of the links of the plurality of pairs of links;
displaying an MRI image of the portion of the patient;
receiving user input that specifies a desired target of the probe;
using the computer system and based on the user input and the determined positions and orientations of the links, moving the probe to a position and orientation relative to the links that avoids interference between the probe and the links as the probe is extended; and
extending the probe into the selected exposed biological tissue between two of the plurality of pairs of links.

6. The method of claim 1, further comprising:
using the computer system, determining the position and the orientation of the probe and determining positions and orientations of the links of the plurality of pairs of links; and
displaying an image of the portion of the patient along with indicia of the position and the orientation of the probe and the positions and the orientations of links.

7. The method of claim 1, wherein the portion of the patient is a breast of the patient, and wherein the first area of exposed biological tissue is a first area of skin of the breast and the second area of exposed biological tissue is a second area of skin of the breast, and wherein the probe includes a biopsy needle, and wherein the method further includes, under the control of the computer, obtaining a biopsy sample of tissue from a lesion in the breast, the method further comprising:
using the computer system, determining the position and the orientation of the probe;
displaying an MRI image of the portion of the patient from a viewpoint of the probe;
using the computer system, determining positions and orientations of the links of the plurality of pairs of links; and
based on the determined position and orientation of the probe and the determined positions and orientations of the links, controlling movement of the probe in order to automatically avoid interference between the probe and the links.

8. An apparatus comprising:
a tissue-compression fixture that includes a plurality of pairs of elongate links including a first pair of links, a second pair of links and an $N^{th}$ pair of links, where N is an integer larger than 2, and wherein each one of the plurality of pairs of links includes:
a first link and a second link, wherein each link of the pair of links has a first end and a second end;
a revolute joint wherein the revolute joint connects a location between the first end and the second end of the first link to a location between the first end and the second end of the second link; and
a plurality of spherical joints that includes a first spherical joint, a second spherical joint, a third spherical joint, and a fourth spherical joint, wherein the first spherical joint is attached to the first end of the first link, the second spherical joint is attached to the second end of the first link, the third spherical joint is attached to the first end of the second link, and the fourth spherical joint is attached to the second end of the second link,
wherein the first and fourth spherical joints of the first pair of links are the third and second spherical joints, respectively, of the second pair of links of a row of the plurality of pairs of links, and the third and second spherical joints of the first pair of links are the first and fourth spherical joints, respectively, of the $N^{th}$ pair of links of the row;
wherein the plurality of pairs of links are configured to be moved to compress bodily tissue of a portion of a patient such that a first area of biological tissue is exposed between the first pair of links and the second pair of links and a second area of biological tissue is exposed between the first pair of links and the $N^{th}$ pair of links, and wherein the fixture is made of at least one material that is compatible with use in an magnetic-resonance-imaging (MRI) machine when the MRI machine is in operation;
an electrically controlled actuator having a receiver for a medical-procedure probe, wherein the electrically controlled actuator is located on a circumference of a first circle that is perpendicular to and surrounding a first rotational axis that passes through the biological tissue, and has a plurality of positional degrees of freedom to position the probe relative to the tissue-compression fixture including a first degree of freedom that varies a first probe coordinate position on the circumference of the first circle and at a first rotational angle relative to the first rotational axis that passes through the bodily tissue in the tissue compression fixture, a degree of freedom that varies a probe height position, a degree of freedom that varies a probe rotational angle relative to a second rotational axis that is not the first rotational axis, a degree of freedom that varies a probe pitch angle, and a degree of freedom that varies a probe insertion depth along a probe-extension line that extends along a longitudinal axis of the probe; and
a computer system operatively coupled to the actuator to control a movement of the probe, wherein the computer is configured to receive MRI image data of the portion of the patient and to receive input user commands, and wherein the computer is configured, based on the obtained MRI image data, to control the actuator to move the medical-procedure probe to a position and an orientation that addresses a selected one of the first area of exposed biological tissue and the second area of exposed biological tissue, and then based on the received user commands, to extend the probe into the selected exposed biological tissue of the portion of the patient.

9. The apparatus claim 8, wherein the portion of the patient is a breast of the patient, and wherein the first area of exposed biological tissue is a first area of exposed skin of the breast and the second area of exposed biological tissue is a second area of exposed skin of the breast, and wherein the probe includes a biopsy needle, and wherein the electrically controlled actuator is configured, under the control of the computer system, to obtain a biopsy sample of tissue from a lesion in the breast.

10. The apparatus claim 9, further comprising:
a display unit operatively coupled to the computer and configured to display an MRI image of the portion of the patient;
an input device operatively coupled to the computer and configured to receive user input that specifies a desired target of the probe relative to the displayed MRI image,
wherein the computer system is configured to determine the position and the orientation of the probe, to determine positions and orientations of the links of the plurality of pairs of links, and wherein the computer system is configured, based on the user input and the determined positions and orientations of the links, to move the probe to a position and orientation relative to the links that addresses a selected one of the first and second areas of exposed skin and that avoids interference between the probe and the links as the probe is extended, and to extend the probe into the selected area of exposed skin between two of the plurality of pairs of links.

11. The apparatus claim 8, wherein the computer system is configured to determine the position and the orientation of the probe, and based on the received MRI image data and the determined position and orientation of the probe to calculate an MRI image of the portion of the patient from a viewpoint of the probe; and wherein the apparatus further includes a display operatively coupled to the computer to display the calculated MRI image of the portion of the patient from a viewpoint of the probe.

12. The apparatus claim 8, wherein the computer system is configured to determine the position and the orientation of the probe, to determine positions and orientations of the links of the plurality of pairs of links; and based on the determined position and orientation of the probe and the determined positions and orientations of the links, to control the actuator to move the probe in order to automatically avoid interference between the probe and the links.

13. The apparatus claim 8, further comprising:
a display unit operatively coupled to the computer;
wherein the computer system is configured to determine the position and the orientation of the probe, to determine positions and orientations of the links of the plurality of pairs of links, and to couple signals to the display unit to display an image of the portion of the patient along with indicia of the position and the orientation of the probe and the positions and the orientations of the links.

14. The apparatus claim 8, further comprising:
a display unit operatively coupled to the computer;
wherein the portion of the patient is a breast of the patient, and wherein the first area of exposed biological tissue is a first area of skin of the breast and the second area of exposed biological tissue is a second area of skin of the breast, and wherein the probe includes a biopsy needle, and wherein the computer is configured to control the actuator to obtain a biopsy sample of tissue from a lesion in the breast,
wherein the computer system is configured to determine positions and orientations of the links of the plurality of pairs of links, and to determine the position and the orientation of the probe, and to display an MRI image of the portion of the patient from a viewpoint of the probe; and based on the determined position and orientation of the probe and the determined positions and orientations of the links, to control the actuator to move the probe in order to automatically avoid interference between the probe and the links.

15. An apparatus comprising:
a tissue-compression fixture having a plurality of pairs of links that are configured to be moved to compress bodily tissue of a portion of a patient from a plurality of at least three directions, wherein the plurality of pairs of links include a first pair of links, a second pair of links and an $N^{th}$ pair of links, where N is an integer larger than 2, and wherein each one of the plurality of pairs of links includes:
a first link and a second link, wherein each link of the pair of links has a first end and a second end;
a revolute joint wherein the revolute joint connects a location between the first end and the second end of the first link to a location between the first end and the second end of the second link; and
a plurality of spherical joints that includes a first spherical joint, a second spherical joint, a third spherical joint, and a fourth spherical joint, wherein the first spherical joint is attached to the first end of the first link, the second spherical joint is attached to the second end of the first link, the third spherical joint is attached to the first end of the second link, and the fourth spherical joint is attached to the second end of the second link,
wherein the first and fourth spherical joints of the first pair of links are the third and second spherical joints, respectively, of the second pair of links of a row of the plurality of pairs of links, and the third and second spherical joints of the first pair of links are the first and fourth spherical joints, respectively, of the $N^{th}$ pair of links of the row;
wherein the fixture is configured such that each of a plurality of areas of biological tissue are exposed between the plurality of pairs of links, and wherein the fixture is compatible with use in an magnetic-resonance-imaging (MRI) machine when the MRI machine is in operation;
an electrically controlled actuator having a receiver for a medical-procedure probe; and
a computer system operatively coupled to the actuator to control a movement of the probe using a plurality of positional degrees of freedom to position the probe relative to the tissue-compression fixture on a circumference of a first circle that is perpendicular to and surrounding a first rotational axis that passes through the biological tissue including a first degree of freedom that determines a first coordinate position of the probe on the circumference of the first circle and at a first rotational angle relative to the first rotational axis that passes through the biological tissue, a second degree of freedom that determines a height of the probe, a third degree of freedom that determines a pitch angle of the probe, a fourth degree of freedom that determines a second rotational angle of the probe relative to a second rotational axis that is not the first rotational axis, and a fifth degree of freedom defined by a probe-extension line that extends along a longitudinal axis of the probe, wherein the computer is configured to receive input user commands, and based on the received user commands, to move the actuator to a selected one of a plurality of different angular positions around the first rotational axis, and heights relative to the tissue-compression fixture, to orient the actuator to the pitch angle and the second rotational angle relative to the tissue-compression fixture, and to then extend the probe along the probe-extension line into biological tissue of the portion of the patient.

16. The apparatus claim 15, wherein the portion of the patient is a breast of the patient, and wherein the exposed plurality of areas of biological tissue include a first exposed area of skin of the breast and a second area of exposed area of skin of the breast, and wherein the probe includes a biopsy needle, and wherein the electrically controlled actuator is configured, under the control of the computer, to obtain a biopsy sample of tissue from a lesion in the breast.

17. The apparatus claim 16, further comprising:
a display unit operatively coupled to the computer and configured to display an MRI image of the portion of the patient;
an input device operatively coupled to the computer and configured to receive user input that specifies a desired target of the probe relative to the displayed MRI image,
wherein the computer system is configured to determine the position and the orientation of the probe, to determine positions and
orientations of the links of the plurality of pairs of links, and wherein the computer system is configured, based on the user input and the determined positions and orientations of the links, to move the probe to a position and orientation relative to the links that addresses a selected one of the first and second exposed areas of skin and that avoids interference between the probe and the links as the probe is extended, and to extend the probe into the selected exposed area of skin between two of the plurality of pairs of links fixture members.

18. The apparatus claim 15, wherein the computer system is configured to determine the position and the orientation of the probe, and based on the received MRI image data and the determined position and orientation of the probe to calculate an MRI image of the portion of the patient from a viewpoint of the probe; and wherein the apparatus further includes a display operatively coupled to the computer to display the calculated MRI image of the portion of the patient from a viewpoint of the probe.

19. The apparatus claim 15, wherein the computer system is configured to determine the position and the orientation of the probe, to determine positions and orientations of the links of the plurality of pairs of links; and based on the determined position and orientation of the probe and the determined positions and orientations of the links, to control the actuator to move the probe in order to automatically avoid interference between the probe and the links.

20. The apparatus claim 15, further comprising a display unit operatively coupled to the computer, wherein the computer system is configured to determine the position and the orientation of the probe, to determine positions and orientations of the links of the plurality of pairs of links, and to couple signals to the display unit to display an image of the portion of the patient along with indicia of the position and the orientation of the probe and the positions and the orientations of the links.

* * * * *